US00RE46383E

(19) United States
(12) Reissued Patent
Jackson

(10) Patent Number: US RE46,383 E
(45) Date of Reissued Patent: May 2, 2017

(54) DECELERATION OF HADRON BEAMS IN SYNCHROTRONS DESIGNED FOR ACCELERATION

(75) Inventor: Gerald Peter Jackson, Lisle, IL (US)

(73) Assignee: HBAR TECHNOLOGIES, LLC, West Chicago, IL (US)

(21) Appl. No.: 11/603,313

(22) Filed: Nov. 20, 2006

Related U.S. Patent Documents

Reissue of:
(64) Patent No.: 6,822,405
Issued: Nov. 23, 2004
Appl. No.: 10/408,866
Filed: Apr. 7, 2003

U.S. Applications:
(63) Continuation-in-part of application No. PCT/US02/27796, filed on Aug. 29, 2002.

(60) Provisional application No. 60/370,605, filed on Apr. 5, 2002, provisional application No. 60/388,428, filed on May 29, 2002, provisional application No. 60/382,042, filed on May 20, 2002, provisional application No. 60/316,711, filed on Aug. 30, 2001.

(51) Int. Cl.

| | |
|---|---|
| ***H05H 15/00*** | (2006.01) |
| ***H05H 11/00*** | (2006.01) |
| ***H05H 13/00*** | (2006.01) |
| ***A61N 5/10*** | (2006.01) |
| ***A61B 6/03*** | (2006.01) |
| ***A61B 6/00*** | (2006.01) |
| ***G21K 5/04*** | (2006.01) |
| ***H05H 13/04*** | (2006.01) |

(52) U.S. Cl.
CPC ..... *A61N 5/10* (2013.01); *A61B 6/037* (2013.01); *A61B 6/4258* (2013.01); *A61N 5/1079* (2013.01); *G21K 5/04* (2013.01); *H05H 13/04* (2013.01); *A61B 6/583* (2013.01); *A61N 5/1048* (2013.01); *A61N 2005/1052* (2013.01); *A61N 2005/1087* (2013.01)

(58) Field of Classification Search
USPC ..... 315/500, 501, 503, 507; 250/492.1, 250/492.3, 493.1, 505.1
See application file for complete search history.

(56) References Cited

U.S. PATENT DOCUMENTS

| | | | | |
|---|---|---|---|---|
| 4,491,948 | A * | 1/1985 | Deacon et al. | 372/2 |
| 4,657,722 | A * | 4/1987 | Bennett | C09K 5/044 376/105 |
| 4,780,683 | A * | 10/1988 | Nakata | 315/503 |
| 5,001,437 | A * | 3/1991 | Miyata et al. | 328/235 |
| 5,051,600 | A | 9/1991 | Schuetz et al. | |
| 5,073,913 | A * | 12/1991 | Martin | 378/34 |

(Continued)

OTHER PUBLICATIONS

Office Action Summary for U.S. Appl. No. 11/702,950, mailed Sep. 15, 2008. pp. 1-7.

(Continued)

*Primary Examiner* — Angela M Lie
(74) *Attorney, Agent, or Firm* — Peter K. Trzyna, Esq.

(57) ABSTRACT

A method for using a synchrotron, the method including the steps of: providing a synchrotron designed to accelerate a hadron beam to higher momenta; altering said synchrotron to enable deceleration of hadron beams to lower momenta; and using the synchrotron in said altering step in decelerating a hadron beam to lower momentum.

67 Claims, 18 Drawing Sheets

(56) References Cited

U.S. PATENT DOCUMENTS

| | | | | | |
|---|---|---|---|---|---|
| 5,138,271 | A * | 8/1992 | Ikegami | 328/233 |
| 5,339,812 | A | 8/1994 | Hardy et al. | 600/429 |
| 5,363,008 | A * | 11/1994 | Hiramoto et al. | 313/62 |
| 5,374,913 | A * | 12/1994 | Pissantezky et al. | 335/216 |
| 5,538,494 | A * | 7/1996 | Matsuda | 600/1 |
| 5,557,178 | A * | 9/1996 | Talman | 315/501 |
| 5,600,213 | A * | 2/1997 | Hiramoto et al. | 315/507 |
| 5,698,954 | A * | 12/1997 | Hirota et al. | 315/503 |
| 5,789,875 | A * | 8/1998 | Hiramoto et al. | 313/505 |
| 5,895,926 | A | 4/1999 | Britton et al. | 250/492.3 |
| 5,969,367 | A * | 10/1999 | Hiramoto et al. | 250/492.3 |
| 5,977,554 | A | 11/1999 | Smith et al. | 250/493.1 |
| 6,160,263 | A | 12/2000 | Smith et al. | 250/493.1 |
| 6,198,957 | B1 | 3/2001 | Green et al. | 600/411 |
| 6,265,837 | B1 * | 7/2001 | Akiyama et al. | 315/503 |
| 6,316,776 | B1 * | 11/2001 | Hiramoto et al. | 250/492.3 |
| 6,414,331 | B1 | 7/2002 | Smith et al. | 250/493.1 |
| 6,433,349 | B2 * | 8/2002 | Akiyama | 250/492.3 |
| 6,462,490 | B1 * | 10/2002 | Matsuda | H05H 7/02 250/492.3 |
| 6,576,916 | B2 | 6/2003 | Smith et al. | 250/493.1 |
| 6,606,370 | B1 * | 8/2003 | Kasprowicz | 376/913 |
| 6,815,688 | B2 | 11/2004 | Schneiker et al. | 250/396 R |
| 6,826,423 | B1 * | 11/2004 | Hardy | A61B 5/064 600/414 |
| 2003/0183783 | A1 | 10/2003 | Smith et al. | 250/493.1 |
| 2004/0096033 | A1 | 5/2004 | Seppi et al. | 378/65 |
| 2004/0162457 | A1 * | 8/2004 | Maggiore | A61N 5/10 600/1 |

OTHER PUBLICATIONS

Amendment and Response for U.S. Appl. No. 11/702,950, filed Feb. 17, 2009. pp. 1-6.

U. Oelfke, G.K.Y. Lam, & M.S. Atkins. Proton Dose Monitoring with PET: Quantitative Studies in Lucite. Received Jun. 29, 1995. 20 pages.

U.S. Appl. No. 60/316,711, filed Aug. 30, 2001, Howe.

U.S. Appl. No. 60/370,605, filed Apr. 5, 2002, Jackson.

U.S. Appl. No. 60/382,042, filed May 20, 2002, Jackson.

U.S. Appl. No. 60/388,428, filed May 29, 2002, Maggiore.

U.S. Appl. No. 60/731,971, filed Oct. 31, 2005, Jackson.

U.S. Appl. No. 60/734,126, filed Nov. 7, 2005, Jackson.

U.S. Appl. No. 60/735,108, filed Nov. 9, 2005, Jackson.

File History for U.S. Appl. No. 10/479,272, filed Dec. 1, 2003, and File History for PCT/US02/27796, filed Aug. 29, 2002. pp. 1-227.

U.S. Appl. No. 10/479,272, "Draft Declaration of Gerald Jackson" 2008.

U.S. Appl. No. 10/479,272, "Draft Declaration of Steven Howe" 2008.

Fermilab Low Energy Antiproton Home Page. Last edited by Gerry Jackson (gpj @fnal.gov) on Oct. 14, 2000. pp. 1-34.

"Improper Change of Inventorship by International Bureau" letter dated Nov. 20, 2006, to WIPO, and WIPO' s "Communication in Cases for Which No Other Form is Applicable" letter dated Jan. 26, 2007, stating that the "removal of inventors Steve Howe and Gerald Jackson was issued in error." pp. 1-4.

Office Action mailed Sep. 15, 2008, for U.S. Appl. No. 11/702,950. pp. 1-23.

Amendment and Response filed on Feb. 17, 2009, for U.S. Appl. No. 11/702,950. pp. 1-6.

R.A. Lewis, G.A. Smith, and S.D. Howe, "Antiproton Portable Traps and Medical Applications", Hyperfine Interactions, vol. 109 (1997) 155.

Gray, L., and Kalogeropoulos, T. E. "Possible Biomedical Applications of Antiproton Beams: Focused Radiation Transfer" Radiat. Res. 97, 246-252 (1984).

Sullivan, A.H., "A Measurement Of The Local Energy Deposition By Antiprotons Coming To Rest In Tissue-Like Material," Phys. Med. Biol., 1985, vol. 30, No. 12, 1297-1303. CERN, Geneva, Switzerland, Received Jun. 5, 1985.

Samuel G. Gilbert, "Office Action—Final Rejection" mailed on Jan. 4, 2011, in U.S. Appl. No. 11/702,950, filed Feb. 5, 2007. pp. 1-9. USA.

Samuel G. Gilbert, "Office Action" mailed on Aug. 18, 2010, in U.S. Appl. No. 11/702,950, filed Feb. 5, 2007. pp. 1-33. USA.

Samuel G. Gilbert, "Office Action—Final Rejection" mailed on Jun. 15, 2009, in U.S. Appl. No. 11/702,950, filed Feb. 5, 2007. pp. 1-9. USA.

Samuel G. Gilbert, "Notice of Allowance" mailed on Sep. 26, 2011, in U.S. Appl. No. 11/702,950, filed Feb. 5, 2007. pp. 1-59. USA.

* cited by examiner

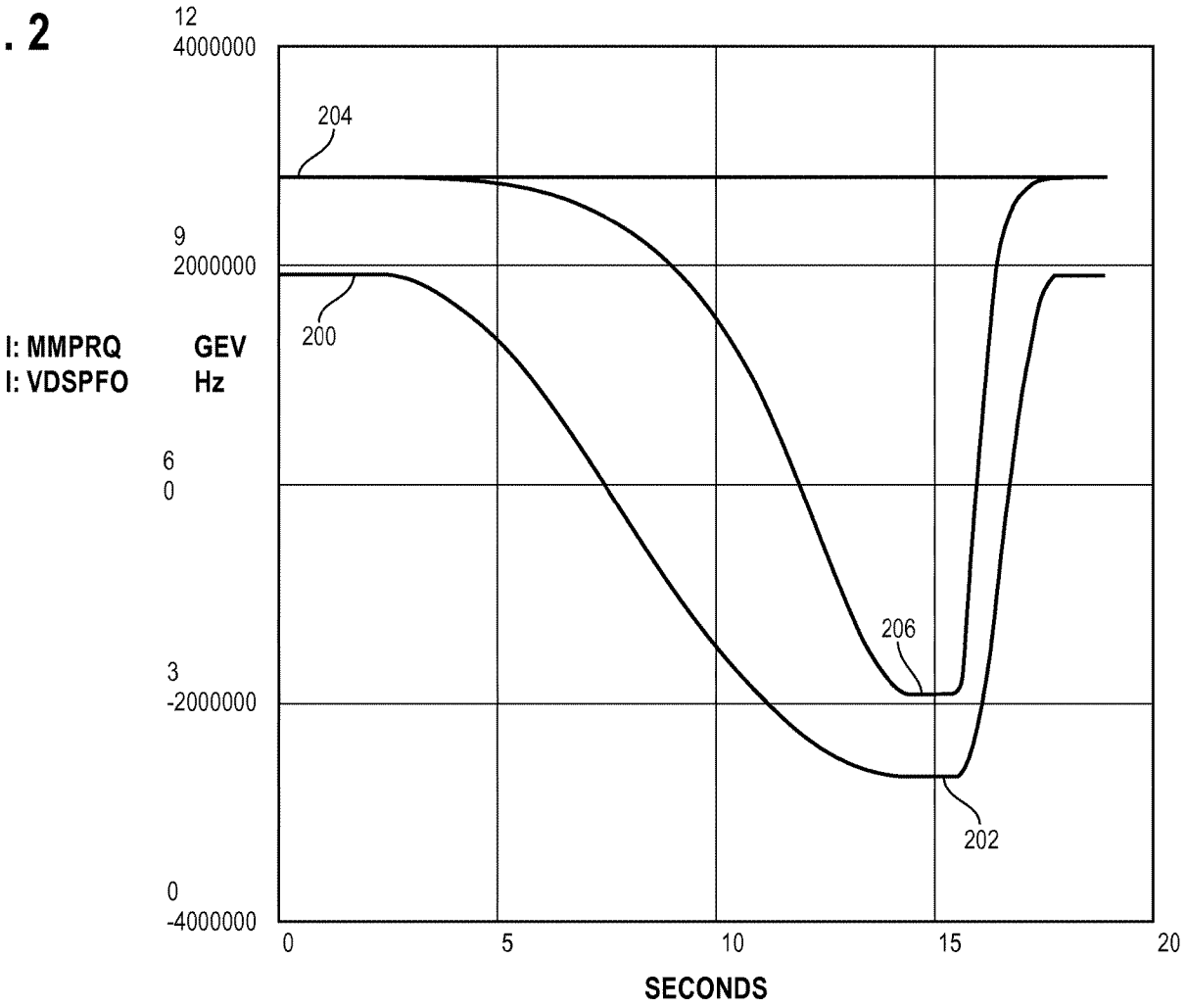
FIG. 2
AMENDED

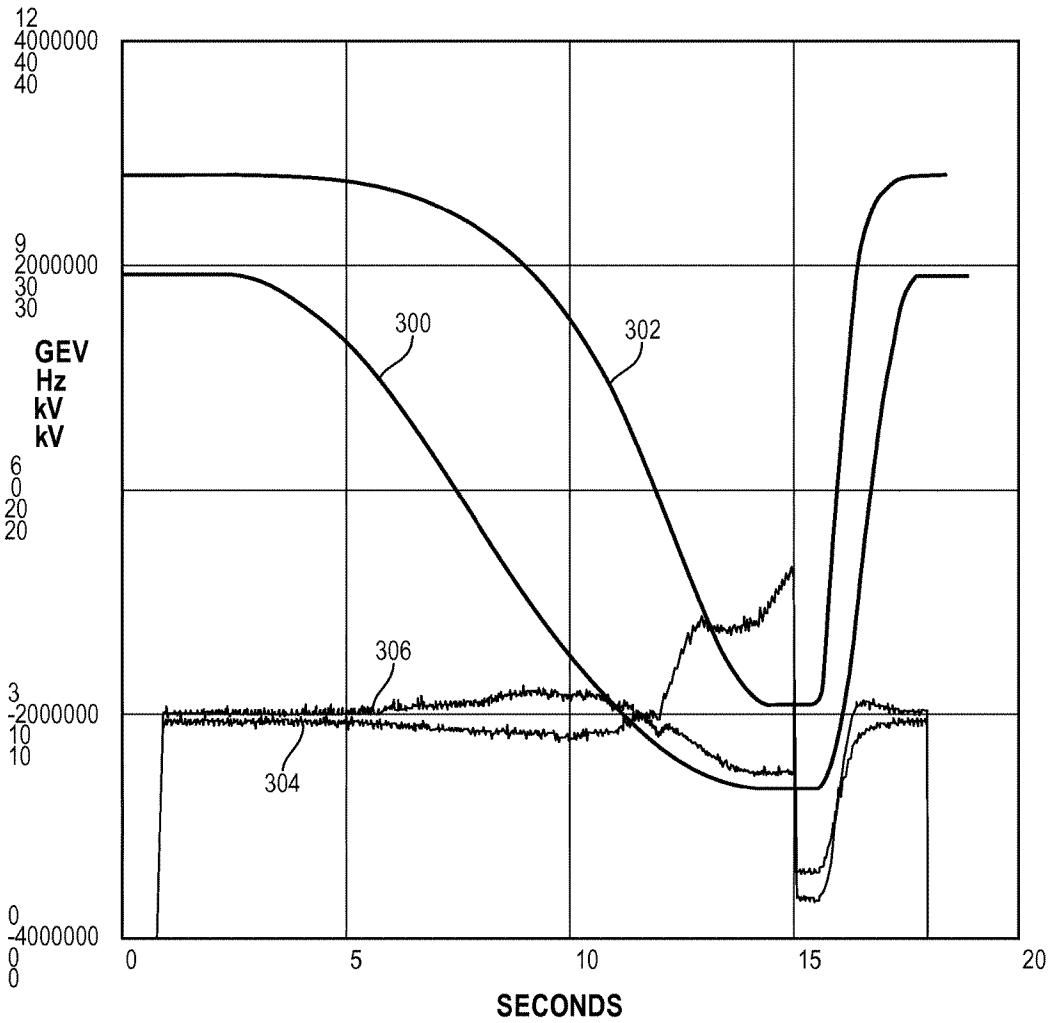
FIG. 3
AMENDED

NEW

NEW

PROTON MULTIPLE SCATTERING AFTER TRAVERSED 15 cm $H_2O$ IS SHOWN.

NEW

PROTON MULTIPLE SCATTERING AFTER TRAVERSING 15 cm $H_2O$ IS SHOWN.

NEW

THE SHOWER RADIAL ENERGY DEPOSITION ORTHOGONAL TO THE SHOWER AXIS IN TUNGSTEN IS SHOWN.

NEW

THE SHOWER RADIAL ENERGY DEPOSITION ORTHOGONAL TO THE SHOWER AXIS IN $PbWO_4$ IS SHOWN.

NEW

THE OPENING ANGLE IN DEGREES AS A FUNCTION OF NEUTRAL PION MOMENTA AND THE RATIO OF GAMMA-RAY ENERGIES ARE SHOWN.

NEW

THE LABORATORY-OPENING ANGLES IN RADIANS FOR THE DECAY GAMMAS FROM THE NEUTRAL PION AS A FUNCTION OF PION MOMENTUM AND THE RATIO OF THE ENERGIES OF THE DECAY GAMMAS ARE SHOWN.

NEW

DECELERATION OF HADRON BEAMS IN SYNCHROTRONS DESIGNED FOR ACCELERATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CONTINUITY STATEMENT

[This patent application is a Provisional, claiming priority from, and incorporated by reference, the following patent applications: "Antiproton Deceleration," Ser. No. 60/370,605, filed Apr. 5, 2002; "Real Time Detention of Delivery of Antiprotons for Therapeutic Use," Ser. No. 60/388,428, filed May 29, 2002; "Method for Investigating Use of Antiproton Beams in Clinical Radiotherapy," Ser. No. 60/382,042 filed May 20, 2002, now abandoned, and "Antiproton Production and Delivery for Imaging and Termination of Undesirable Cells" Ser. No. PCT/US02/27796, which in turn claims priority from a patent application Ser. No. 60/316,711 "Non-invasive Method of Cellular Termination Using Antiproton Reactions" filed Aug. 30, 2001, incorporated by reference.] *The present patent application claims priority pursuant to 35 U.S.C. Sec. 120 and 35 U.S.C. Sec. 365(c), is a reissue of Ser. No. 10/408,866, filed Apr. 7, 2003, issued as U.S. Pat. No. 6,822,405 on Nov. 23, 2004, and claims benefit from the following patent applications: Ser. No. 60/370,605, filed Apr. 5, 2002, Ser. No. 60/388,428, filed May 29, 2002, and Ser. No. 60/382,042 filed May 20, 2002. The present application also claims benefit from Ser. No. PCT/US02/27796, filed Aug. 29, 2002, which in turn claims benefit from Ser. No. 60/316,711 filed Aug. 30, 2001, Ser. No. 60/370,605, filed Apr. 5, 2002, Ser. No. 60/388,428, filed May 29, 2002, and Ser. No. 60/382,042 filed May 20, 2002. All of the provisional patent applications and the PCT application are incorporated by reference.*

BACKGROUND OF THE INVENTION

A. Field of the Invention

This invention relates to the field of hadron beams in synchrotrons designed for acceleration. More particularly, the present invention relates to a method for decelerating hadron beams using existing synchrotrons designed for acceleration. Even more specifically, the present invention relates to a method for decelerating antiprotons using existing synchrotrons designed for acceleration. More specifically, the present invention addresses the production of antiprotons; the collection and storage of antiprotons; the transport of antiprotons.

B. Background of the Invention

Hadron beams are typically accelerated using synchrotrons, cyclotrons, or linear accelerators. For example, at the Loma Linda proton therapy facility a synchrotron is employed once the protons are emitted by the ion source and pre-accelerated in a radio-frequency quadrupole (RFQ), while the Massachussetts General Hospital proton therapy facility employs a cyclotron. They accelerate protons up to a momentum of 0.73 GeV/c, which corresponds to the energy a proton needs to completely traverse a typical human chest cavity.

There are examples of synchrotrons specifically designed for deceleration of hadron beams. These include the LEAR and AD synchrotrons, both operated at the CERN particle physics laboratory in Geneva, Switzerland. These synchrotrons are used to perform scientic experiments with antiprotons.

A third category of synchrotrons, called storage rings, neither accelerate nor decelerate hadron beams to higher or lower momenta. Their purpose is to merely store the hadron beam at their original injection momentum.

Because the radius of curvature of a hadron beam traversing bending magnets is proportional to the beam momentum, and the cost of the synchrotron scales with its circumference, the synchrotron is designed such that the bending (dipole) magnets are at their maximum field strength at the maximum anticipated momentum. Therefore, storage rings always operate at the maximum strength of their magnets, while accelerating synchrotrons operated at maximum magnetic field strength only at the end of the acceleration process.

All mechanical and electrical systems have a finite dynamic range within which the components can operate. The same is true of synchrotrons. Due to limitations in magnetic material properties, power supply regulation, and radio frequency acceleration system frequency adjustability, synchrotrons traditionally are found to have a maximum momentum range of a factor of twenty. There is a great deal of literature devoted to this issue in the field of accelerator physics. This reality also explains why laboratories working in the fields of atomic, nuclear, and particle physics have accelerator chains composed of many synchrotrons. The Fermi National Accelerator Laboratory is an example, wherein there are three synchrotrons required to accelerate protons and antiprotons to a momentum of 950 GeV/c for particle physics research. The maximum momentum range of any of these synchrotrons is a factor of 17.

SUMMARY OF THE INVENTION

One aspect of the present invention has an object of providing a means to better decelerate hadron beams. The corresponding method for decelerating antiprotons opens many commercial applications. For example, antiproton irradiation has utility in a variety of fields, including the treatment of cancerous tissue and the generation of radioisotopes within the body that are useful for imaging techniques and therapeutic treatment. In the present invention deceleration is implemented using a synchrotron.

A synchrotron is comprised of a ring of dipole magnets interspersed with quadrupole, sextupole, correction dipole magnets, and one or more radio frequency acceleration systems, the operation of which are all managed by a computer control system. The dipole magnets bend a hadron beam into a closed loop that repeatedly passes through the electromagnetic fields generated by the radio frequency acceleration system. Typically all dipole magnets are wired in series to ensure that every magnet has exactly the same electrical current, and therefore magnetic field strength, in it. One or more power supplies around the synchrotron are employed to provide this electrical current. The amount of electrical current generated by a power supply at any given momentum is determined by commands from the computer control system.

The quadrupole magnets, which focus and defocus the hadron beam in a fashion very similar to the concave and convex lens combination in a telephoto camera lens, make sure that the beam oscillates around the middle of the magnets rather than straying out of the synchrotron. The strength of the focusing and defocusing magnetic fields are adjusted to maintain a desired number of horizontal and vertical oscillations each turn (revolution) around the synchrotron. Typically all of the focusing quadrupoles are wired in series to ensure that every magnet has exactly the same electrical current and hence magnetic field strength. Similarly, all of the defocusing quadrupoles are also wired in series. Two or more power supplies around the synchrotron are employed to provide these two electrical currents. The amount of electrical current generated by a power supply at any given momentum is determined by commands from the computer control system.

The sextupole magnets are used to control the horizontal and vertical chromacities of the synchrotron. Every hadron beam has some non-zero momentum distribution width. Without sextupoles, every hadron with a different momentum would have a different number of horizontal and vertical oscillations per revolution, or horizontal and vertical tunes. The change in tune per unit change in momentum is called chromaticity. The natural chromaticity of a synchrotron without sextupoles is equal and opposite to the tune. But too keep the hadron beam in the synchrotron for the desired duration, it is necessary to impose sextupole magnetic fields that simultaneously reduce both the horizontal and vertical chromaticity to near zero. Typically there is one sextupole placed near every quadrupole, with sextupoles near focusing quadrupoles having one field and the sextupoles near defocusing quadrupoles having a nearly equal but opposite field. Typically, all of the focusing "focusing" sextupoles are wired in series to ensure that every magnet has exactly the same electrical current and hence magnetic field strength. Similarly, all of the "defocusing" sextupoles are also wired in series. Two or more power supplies around the synchrotron are employed to provide these two electrical currents. The amount of electrical current generated by a power supply at any given momentum is determined by commands from the computer control system.

The position and orientation of each magnet always has some tolerance of misalignment. In addition, the strength of every dipole magnet is not precisely equal. These accumulated errors cause the hadron beam to deviate away from the magnet centers. Dipole correction magnets are used to steer a hadron beam vertically and horizontally, correcting the overall beam trajectory. There is typically one horizontal dipole corrector magnet at each focusing quadrupole and one vertical dipole corrector magnet at each defocusing quadrupole. Because the distribution of errors is typically random and time variable, each dipole corrector magnet has a unique electrical current generated by a separate power supply. The amount of electrical current generated by a power supply at any given momentum is determined by commands from the computer control system.

In a linear accelerator, each hadron in the beam passes once through each radio frequency acceleration cavity supporting electromagnetic fields. Just as a surfer rides the edge of a wave to pick up speed, each charged hadron is accelerated or decelerated by riding either the leading or trailing edge of the electromagnetic waves. Each cavity and the multiple radio frequency amplifiers that power them are some of the most expensive elements of any particle accelerator. The innovation behind synchrotrons is that the hadron beam is looped around to reuse the same cavities multiple times, receiving momentum changes tens or hundreds of thousands of time per second. In this way, larger overall momentum changes are implemented at a fraction of the cost if implemented using a linear accelerator.

The importance of this invention, the modifying of a synchrotron designed for hadron beam acceleration in order to decelerate hadron beams, is the immense savings in time, manpower, and money over designing and building a dedicated synchrotron for deceleration. Whereas the construction of a new synchrotron can cost anywhere between $10 million and $1 billion, depending on the maximum momentum required, this modification of an existing synchrotron can cost as little as $10,000.

These and other features, objectives and advantages of the present improved invention will be readily understood upon consideration of the following detailed description of certain embodiments of the present improved invention and the accompanying drawings.

However, as a summary overview, the present invention provides a method for modifying an existing synchrotron designed for the acceleration of hadron beams to higher momenta, such that the synchrotron is enabled to decelerate hadron beams instead to lower momenta. These modifications can be made, for example, to certain synchrotron equipment and computer control system hardware and software to produce a counterintuitive use of a synchrotron designed for accelerating, i.e., decelerating.

Currently, antiprotons are generated and used in experimental studies of elementary particles physics. These experiments are typically performed at large particle accelerators, such as the Tevatron at the Fermi National Accelerator Laboratory (Fermilab). The Fermilab accelerator complex includes various linear accelerators and synchrotrons that are designed to generate antiprotons, to accelerate these antiprotons to very high energies and momenta (typically to 1 TeV), and to collide these antiprotons together with protons. The results of the collisions can be analyzed to provide information regarding the structure and physical laws of the universe.

While these experimental studies of particle physics use antiprotons with very high energies and momenta, other uses of antiprotons, such as the medical use, have relatively small energies and momenta. If the existing sources of antiprotons at such accelerators are to be used as sources of antiprotons for these other fields, the antiprotons have to be decelerated (i.e., energy and momentum of the antiprotons will have to be reduced). In addition, to provide antiprotons to locations that are off-site from the particle accelerators, the antiprotons have to be decelerated sufficiently to enable them to be stored in a portable synchrotron or cyclotron, or trapped in a container and transported to other locations. Because antiprotons are annihilated upon contacting matter, development has been performed to develop adequate containers (e.g., Penning traps) for transporting antiprotons. Further details regarding such methods are incorporated by reference, including: "Container for Transporting Antiprotons," U.S. Pat. No. 5,977,554 issued to Gerald A. Smith, et al. on Nov. 2, 1999; "Container for Transporting Antiprotons," U.S. Pat. No. 6,160,263 issued to Gerald A. Smith, et al. on Dec. 12, 2000.

Embodiments of the present invention decelerate the antiprotons by operating existing particle accelerators, which were designed to accelerate the antiprotons, under conditions that actually reduce the energy and momentum of the antiprotons. In sum, though, there is a method of decelerating antiprotons, the method comprising the steps of: providing antiprotons to a particle accelerator ring, the antiprotons having a first momentum distribution with a first average momentum; operating the particle accelerator ring so as to apply electromagnetic fields to the antiprotons as the antiprotons travel around the ring; and selectively applying the electromagnetic fields to the antiprotons as the antiprotons travel around the ring, such that the antiprotons have a second momentum distribution with a second average momentum less than the first average momentum. Another embodiment of this same idea can be phrased as a method for decelerating antiprotons includes providing antiprotons to a particle accelerator ring. The antiprotons have a first momentum distribution with a first average momentum. The method further includes operating the particle accelerator ring so as to apply electromagnetic fields to the antiprotons as the antiprotons travel around the ring. The method further includes selectively applying the electromagnetic fields to the antiprotons as the antiprotons travel around the ring such that the antiprotons have a second momentum distribution with a second average momentum less than the first average momentum.

BRIEF DESCRIPTION OF THE DRAWINGS

FIG. 2 is beam momentum (I:MMPRQ) and radio frequency acceleration system frequency (I:VDSPF0) vs. time.

FIG. 3 is beam momentum (I:MMPRQ), radio frequency acceleration system frequency (1:VDSPF0), and radio frequency acceleration system electromagnetic field amplitude (I:H28SUM and I:H28F0) vs. time.

DESCRIPTION OF THE PREFERRED EMBODIMENT

Figure 1:
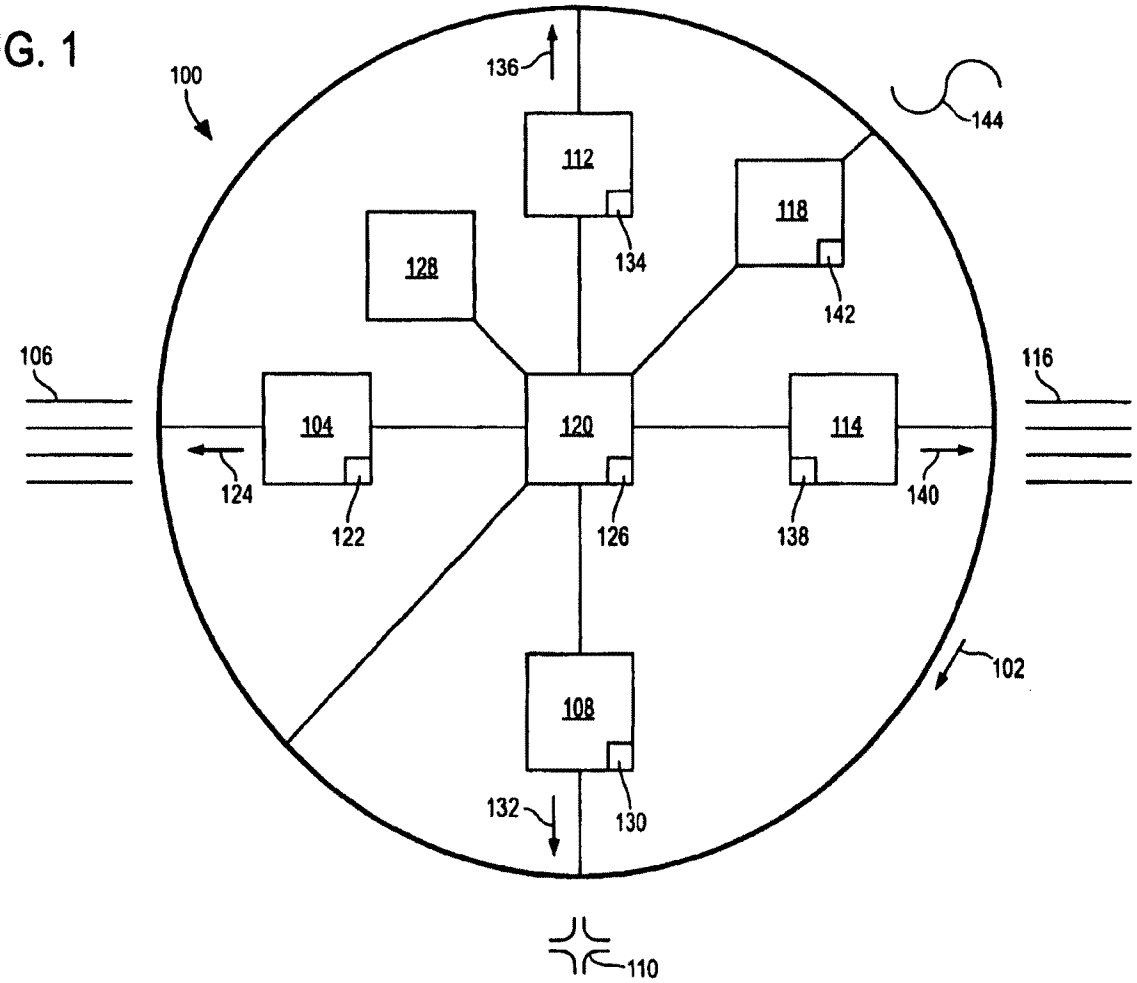
FIG. 1 is a schematic representation of a synchrotron in accordance with the present invention.

FIG. 1 shows a synchrotron 100 designed to accelerate a hadron beam 102 to higher momenta. A method of altering the synchrotron to enable the unanticipated operation of decelerating said hadron beam to lower momenta is the subject of this invention. This method of altering can include modifying a dipole power supply system 104 in order to reduce the strength of a dipole magnetic field 106 during the decelerating of the hadron beam; modifying a quadrupole power supply system 108 in order to reduce the strength of focusing and defocusing magnetic fields 110 during the decelerating of the hadron beam; modifying a sextupole power supply system 112 in order to maintain chromaticity control during the decelerating of the hadron beam; modifying a dipole corrector power supply system 114 in order to reduce the strength of a trajectory correction magnetic field 116 during the decelerating of the hadron beam; modifying a radio frequency acceleration system 118 to impose phase stable momentum reduction during the decelerating of the hadron beam; and modifying a computer control system 120 of the synchrotron to enable the decelerating of the hadron beam.

FIG. 2 shows the result of a proton injected into the synchrotron at the nominal injection momentum 200. After the method of altering the synchrotron 100 is completed, the proton beam is decelerated to a lower momentum 202.

Figure 6:
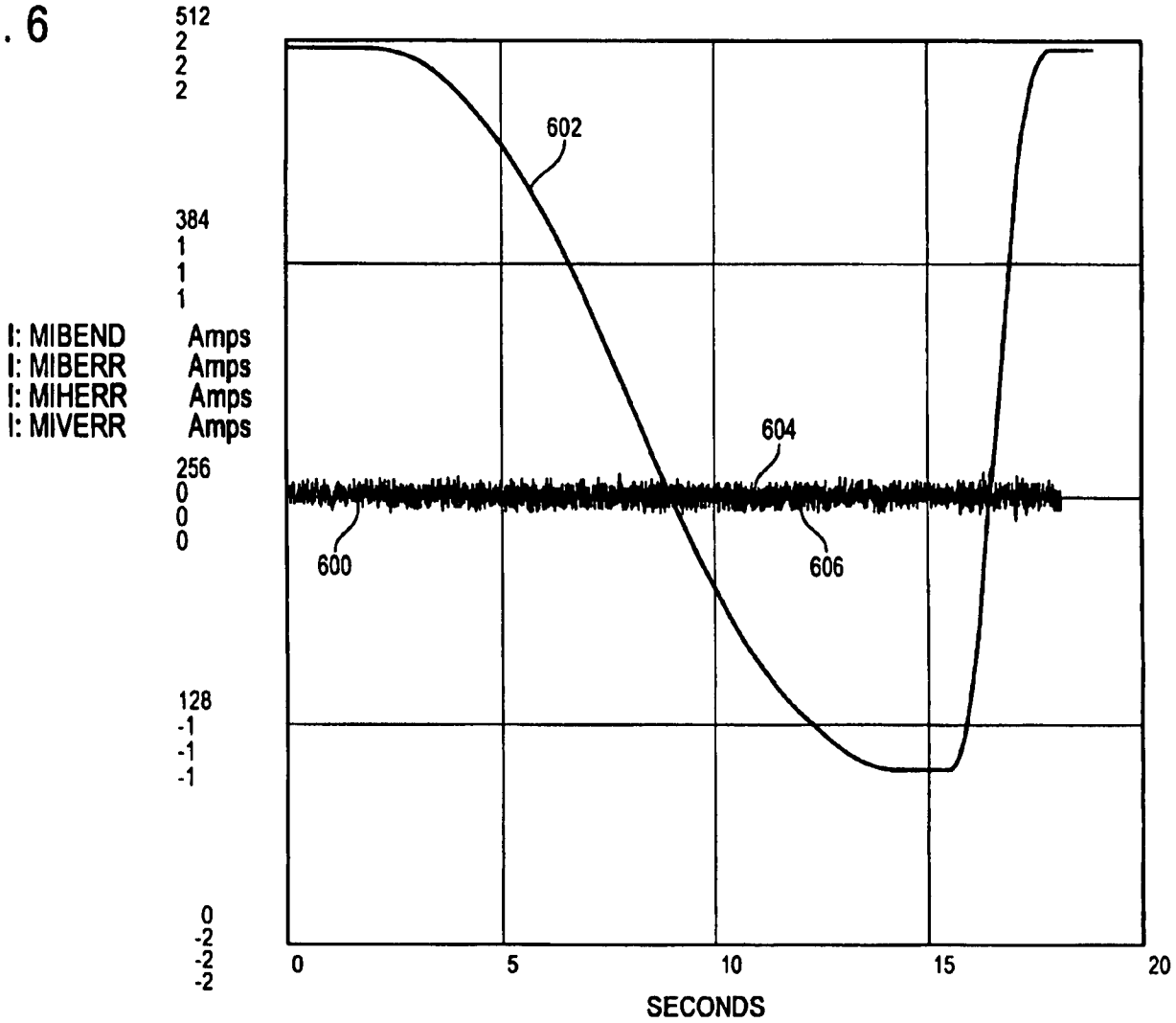
FIG. 6 is dipole power supply system electrical current (I:MIBEND), dipole power supply system error signal (I:MIBERR), focusing quadrupole power supply system error signal (I:MIHERR), and defocusing quadrupole power supply system error signal (I:MIVERR) vs. time.

The step of modifying a dipole power supply system 104 can include adding, removing, or altering a dipole power supply component 122 to ensure that the electric current 124 from the dipole power supply system follows commands from a computer control system 26. It can also include the adding, removing, or altering a computer control system component 126. It can also include the altering of a value of a variable in a computer control system database 128. In one embodiment of this invention, the step of modifying is performed in order to ensure that the dipole power supply error signal 600, the difference between the input command and output current 602 named I:MIBERR in FIG. 6, remains small over many hours.

Figure 9:
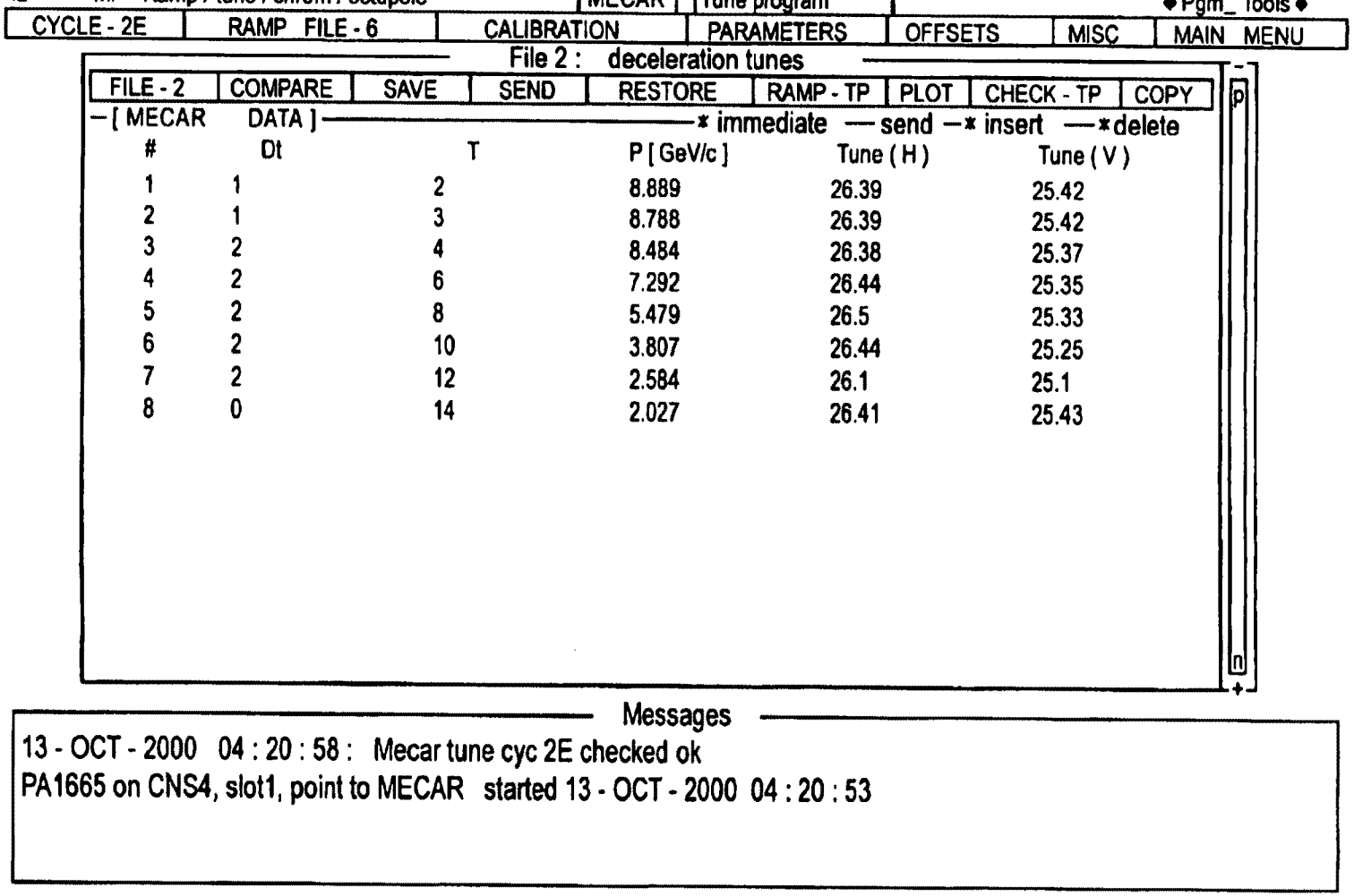
FIG. 9 is a modified instruction set in two quadrupole power supply control system interface cards that enables control of focusing and defocusing magnetic fields during decelerating of a beam.

The step of modifying a quadrupole power supply system 108 can include adding, removing, or altering a quadrupole power supply component 130 to ensure that the electric current 132 from the quadrupole power supply system follows commands from a computer control system 126. It can also include the adding, removing, or altering a computer control system component 126. It can also include the altering of a value of a variable in a computer control system database 128. In one embodiment of this invention, the step of modifying is performed in order to ensure that the quadrupole power supply error signals (604 for the focusing quadrupole power supply I:MIHERR and 606 for the defocusing quadrupole power supply I:MIVERR), the difference between the input command and output current, remain small over many hours. FIG. 9 demonstrates one embodiment of this invention in which computer control system variables are modified in order to control two quadrupole power supplies during the decelerating of a proton beam.

The step of modifying a sextupole power supply system 112 can include adding, removing, or altering a sextupole power supply component 134 to ensure that the electric current 136 from the sextupole power supply system follows commands from a computer control system 126. It can also include the adding, removing, or altering a computer control system component 126. It can also include the altering of a value of a variable in a computer control system database 128.

Figure 4:
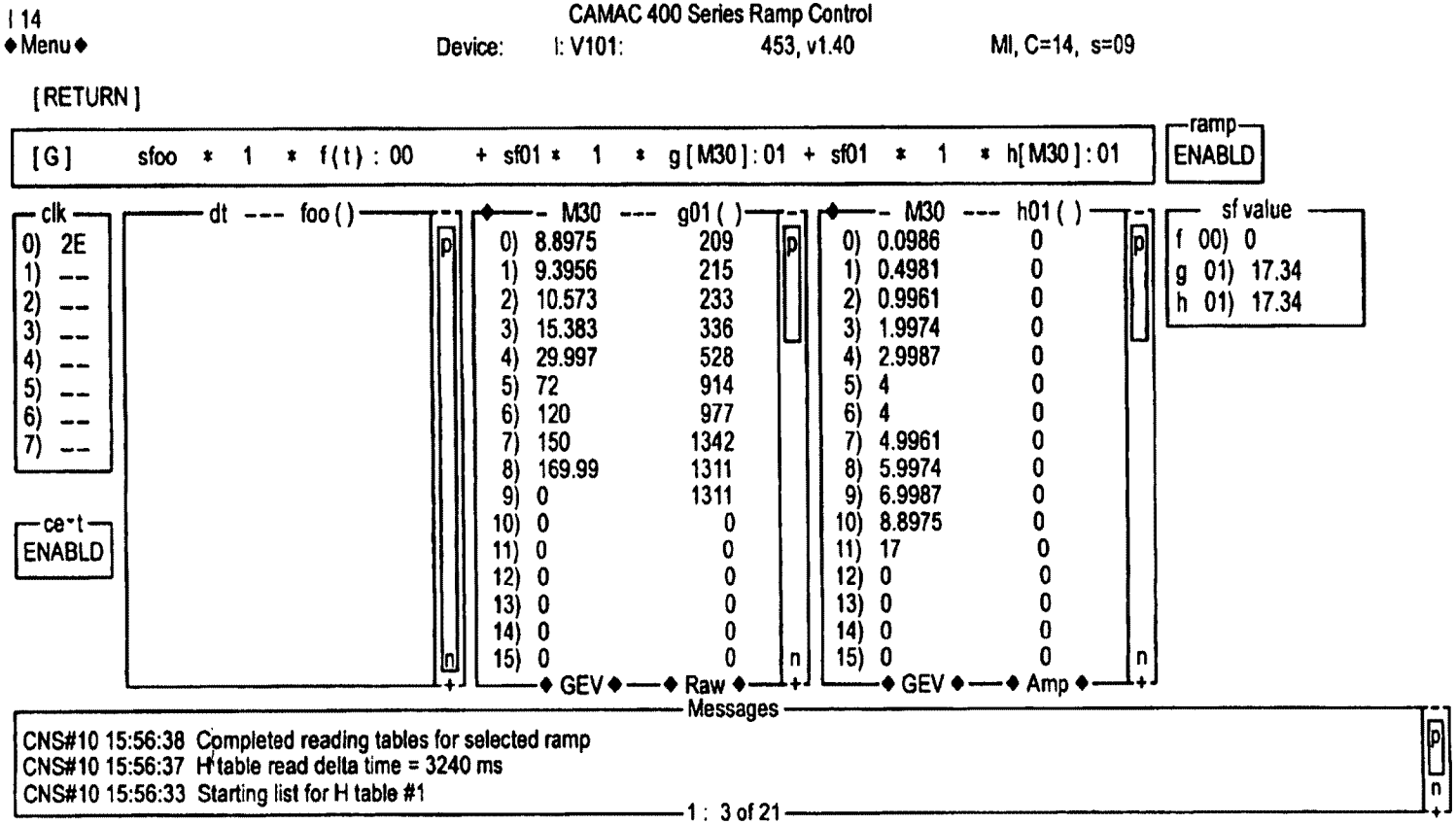
FIG. 4 is a modified instruction set in a dipole corrector power supply system (I:V101) control system interface card that enables control of the beam trajectory during decelerating of a beam.

The step of modifying a dipole corrector power supply system 114 can include adding, removing, or altering a dipole corrector power supply component 138 to ensure that the electric current 140 from the quadrupole power supply system follows commands from a computer control system 126. It can also include the adding, removing, or altering a computer control system component 126. It can also include the altering of a value of a variable in a computer control system database 128. In one embodiment of this invention, the step of modifying is performed in order to ensure that the dipole corrector power supply system can move the hadron beam around any obstruction or misalignment of the synchrotron at any time during the decelerating of the hadron beam. FIG. 4 demonstrates how computer control system variables can be modified in order to control the dipole corrector power supply electric current 500 shown in FIG. 5 used to create a trajectory correction magnetic field 116.

The step of modifying a radio frequency acceleration system 118 can include adding, removing, or altering a radio frequency acceleration system component 142 to ensure that an electromagnetic field 144 of the radio frequency acceleration system follows commands from a computer control system 126. It can also include the adding, removing, or altering a computer control system component 126. It can also include the altering of a value of a variable in a computer control system database 128. In one embodiment of this invention, a modified radio frequency acceleration system 118 is instructed by a modified computer control system 120 to proportionally follow the frequency 204 at which a proton beam circulates around the synchrotron. This frequency decreases as the hadron beam momentum decreases, and reaches a minimum value 206 when the hadron beam momentum has reached its minimum value 202. FIG. 3 shows the result of protons decelerated in the Fermi National Accelerator Laboratory Main Injector synchrotron. The momentum of the proton beam 300 is decelerated over a time duration of 15 seconds. During this time the modified radio frequency acceleration system 118 is generating electromagnetic fields 144 used to decelerate the proton beam and changing its frequency to track the change in proton beam revolution frequency around the Main Injector synchrotron. Extensive modifications to the radio frequency acceleration system 118 and the computer control system 120 were performed in order to keep the magnitude of said electromagnetic fields constant during the 15 seconds. Two measures 304 and 306 of this magnitude are monitored in FIG. 3.

Figure 7:
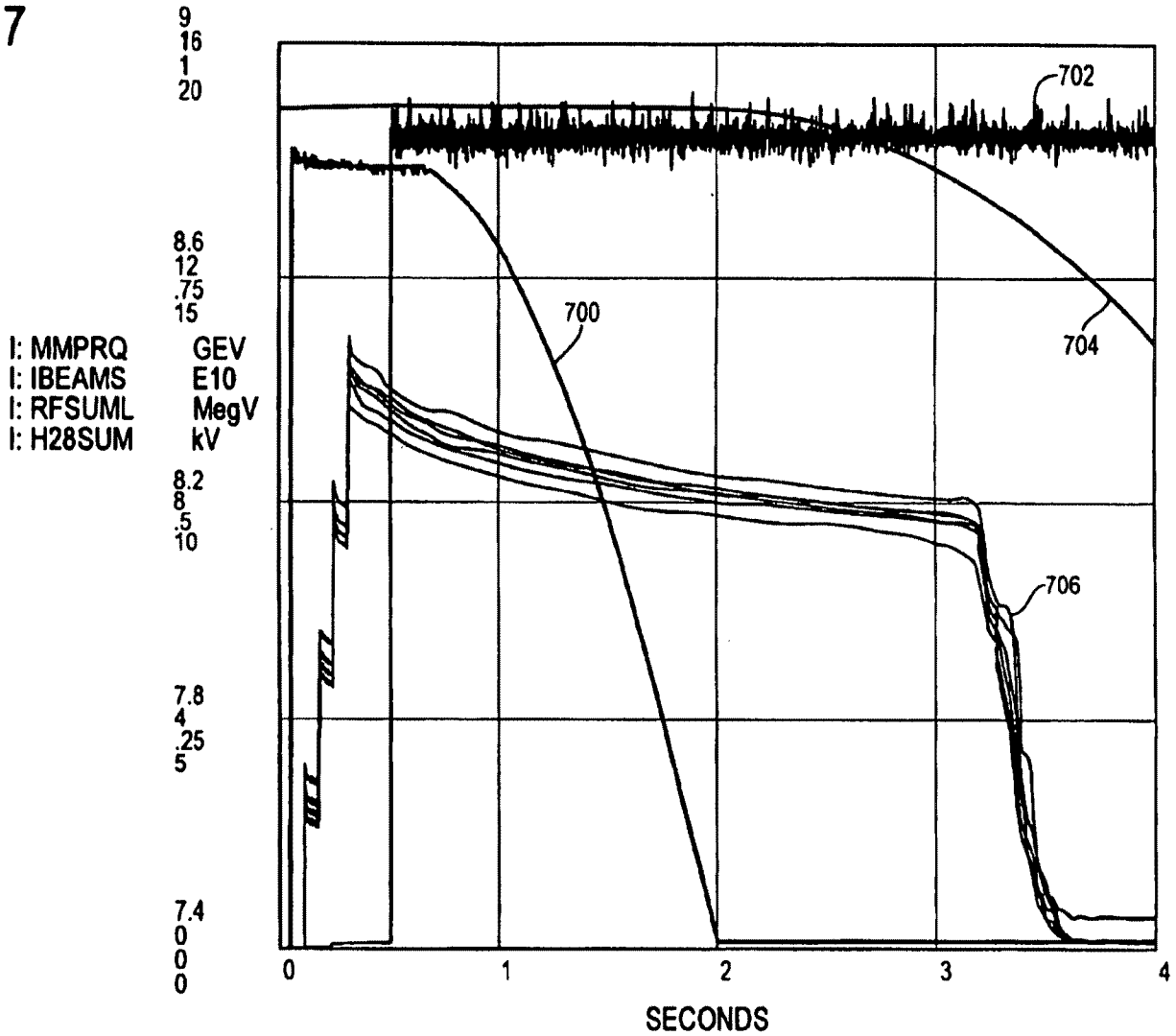
FIG. 7 is radio frequency acceleration system electromagnetic field amplitude (I:RFSUML) used to capture the beam when injected into the synchrotron, radio frequency acceleration system electromagnetic field amplitude (I:H28SUM) used to decelerate the beam, beam momentum (I:MMPRQ), and number of beam particles (beam intensity) in the synchrotron (I:IBEAMS) vs. time.

In another embodiment of this invention, the hadron beam is injected into the synchrotron and controlled by one radio frequency acceleration system and manipulated before the decelerating of the hadron beam begins. FIG. 7 shows such an operation, in which one radio frequency acceleration system has a high initial amplitude 700 that is then gently turned off while the decelerating radio frequency acceleration system is left at a constant amplitude 702 even while the beam momentum 704 is starting to decrease. If modifications to the radio frequency acceleration systems and computer control system 120 are not implemented correctly, the of hadrons circulating in the synchrotron (called intensity 706) will suddenly decrease during the decelerating of the hadron beam.

Figure 8:
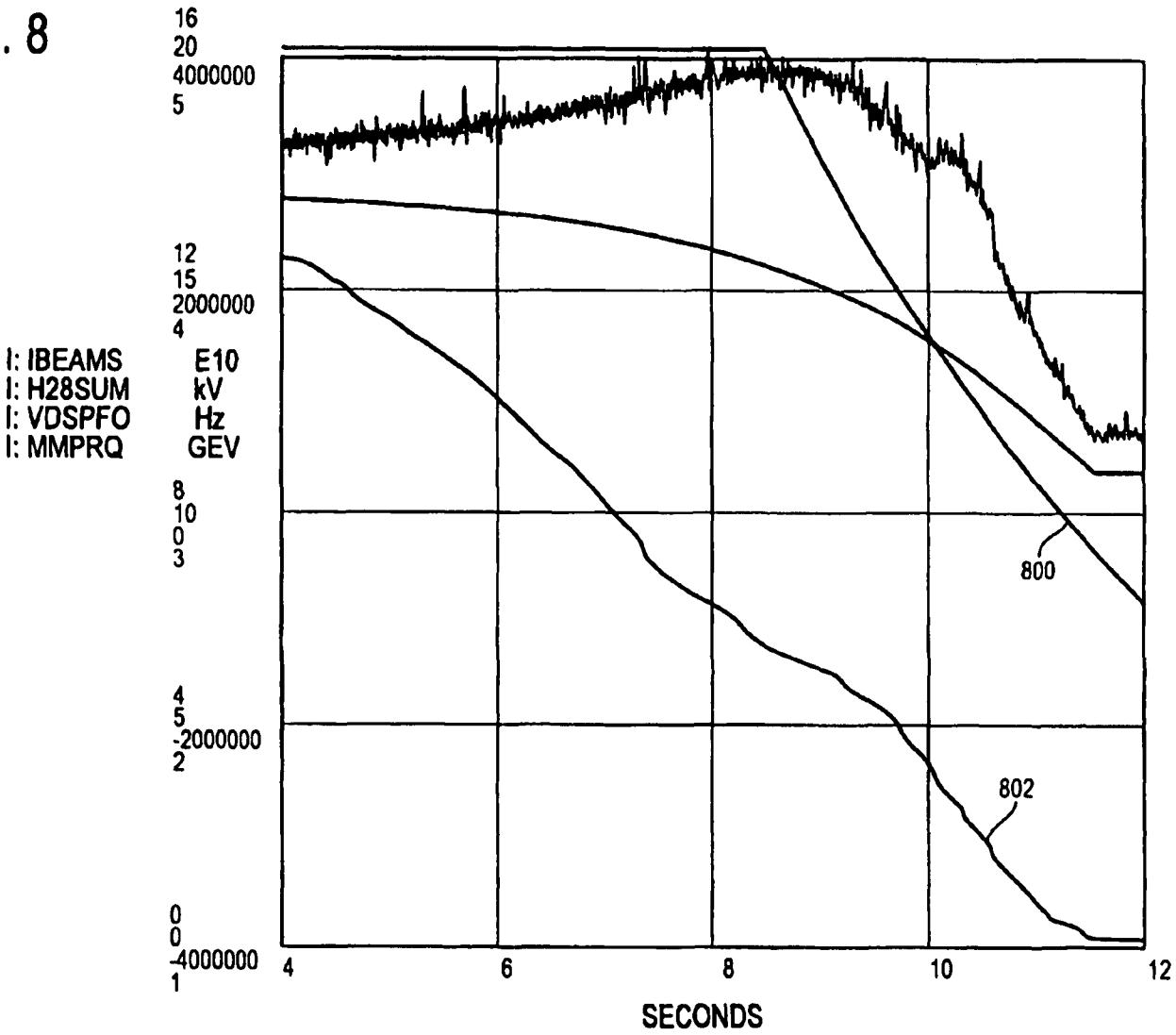
FIG. 8 is beam momentum (I:MMPRQ) and beam intensity (I:IBEAMS) vs. time.

FIG. 8 shows the result of protons decelerated in the Fermi National Accelerator Laboratory Main Injector synchrotron from an initial momentum of 8.889 GeV/c down to 3 GeV/c. At a momentum 800 of 3 GeV/c, labeled I:MMPRQ, the proton beam intensity 802 labeled I:IBEAMS has not yet fallen to zero. Therefore, a small percentage of protons survived a reduction in momentum of almost a factor of three. The cause of this loss of protons during the decelerating of the beam is understood and will be corrected in future decelerations.

When a synchrotron is designed, the first specifications are the minimum and maximum beam momentum. Dipole magnets have a maximum magnetic field. Because the radius of curvature of a hadron beam is proportional to momentum, the radius of the synchrotron is dictated by the maximum magnetic field and the maximum design momentum. On the other hand, dipole magnets have a minimum magnetic field that is determined by the quality of the steel used in its construction. As children find when rubbing steel against a magnet, steel picks up a remnant magnetic field that so distorts the quality of the bending field with uncontrolled quadrupole, sextupole, and higher order field components that cause the beam to fall out of the synchrotron. As a rule of thumb, the limit in the range of momentum in a synchrotron is a factor of 20.

For example, at the Fermi National Accelerator Laboratory (Fermilab) there are three synchrotrons designed to accelerate hadron beams. The Booster has a design minimum (injection) momentum of 0.64 GeV/c and a maximum momentum of 8.9 GeV/c, for an overall momentum range of 14. The Main Injector has a design injection momentum of 8.9 GeV/c and a maximum momentum of 150 GeV/c, for an overall momentum range of 17. Finally, the Tevatron has a design injection momentum of 150 GeV/c and a maximum momentum of 1000 GeV/c, for an overall momentum range of 6.7.

Figure 16:
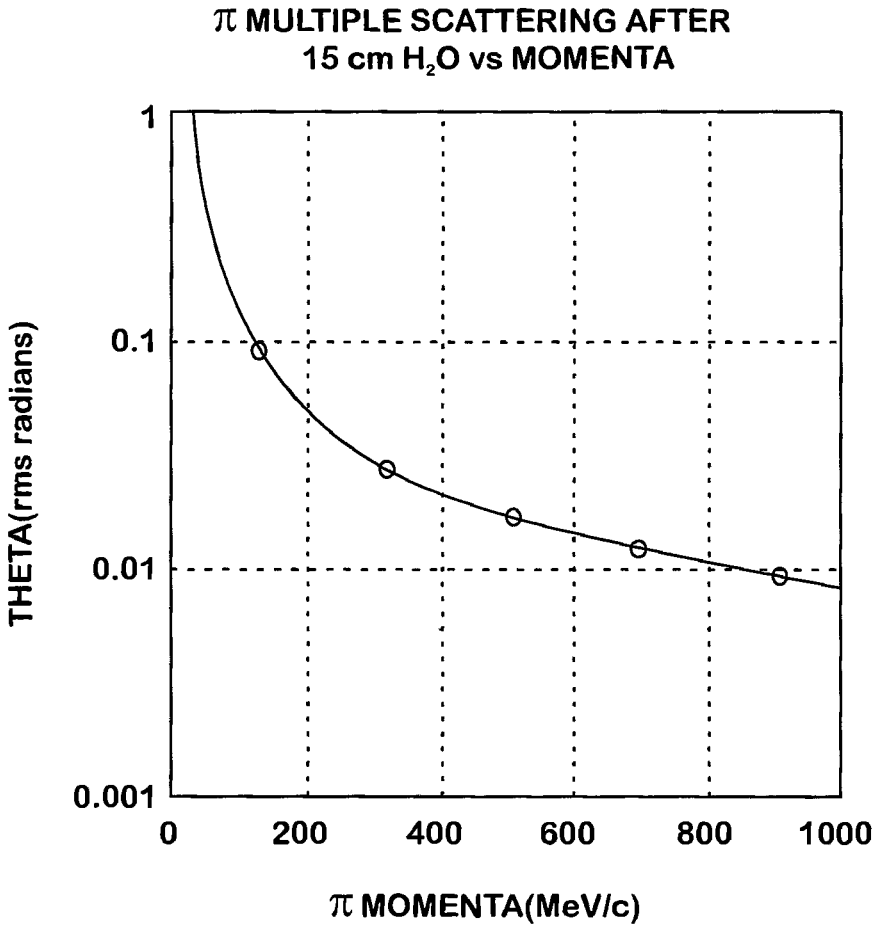
*FIG. 16, which is incorporated by reference from Ser. No. 60/388,428, filed Sep. 29, 2002, is a chart showing $\pi$ multiple scattering after 15 cm H2O vs. Momenta.*

Due to the above magnet limitations, any proposal to inject a hadron beam into an existing synchrotron designed to accelerate beams and then decelerate that beam is greeted with skepticism. For example, in the case of the Fermilab Main Injector one embodiment of this invention has resulted in a demonstrated record synchrotron momentum range of 3 GeV/c to 150 GeV/c, or a factor of 50. Another significant problem with retroactively modifying such a synchrotron to decelerate is the dipole power supply. The amount of electrical current generated by the power supply is proportional to the beam momentum. Therefore, the maximum electrical current is set by the maximum design momentum. In order to decelerate, the dipole power supply system should be capable of generating a noise-free and stable electrical current very near the off-state of the supply, a criteria that the electrical engineers specifying the system never incorporated into their design. Modifications such as the addition, removal, or alteration of filters, regulators, feedback parameters, and control system interface modules should be identified, implemented, and tested. Despite repeated initial misgivings by the designing electrical engineers, FIG. 16 shows the first successful implementation of such modifications, wherein a Fermilab dipole power supply system designed for a maximum electrical current of approximately 9000 Amperes is altered to generate a noise-free and stable current of roughly 100 Amperes.

Quadrupole and sextupole magnets suffer from the same range restrictions in their magnetic field strengths. In addition, their power supplies also generate electrical currents that are roughly proportional to the beam momentum, and hence have the same potential regulation problems as their electrical current are reduced down below their design minimum values. Each power supply needs to be individually assessed and modified in order to generate noise-free and stable electrical current to keep the hadron beam revolving around the synchrotron during the deceleration process.

As shown in FIG. 9, the computer control system that directly commands all elements of the synchrotron should also be modified in order to allow the unanticipated mission of decelerating hadron beams. In this example, the horizontal and vertical tunes are entered by the synchrotron operator from a computer program whose image is in the figure. Normally, the momentum values in the fourth column are ascending in value and with time. In this case, the computer control system database was edited to reflect the reduction in momentum. The computer program was changed to allow for decreasing momentum values and any values below 8.889 GeV/c. The novel aspect of these changes is that unused capabilities of the computer control system hardware were identified wherein the modification did not affect the dozens of other computer programs and control system subsystems that utilized the same hardware. In this way much less effort and disruption to synchrotron operations is used to implement hadron beam deceleration.

Figure 5:
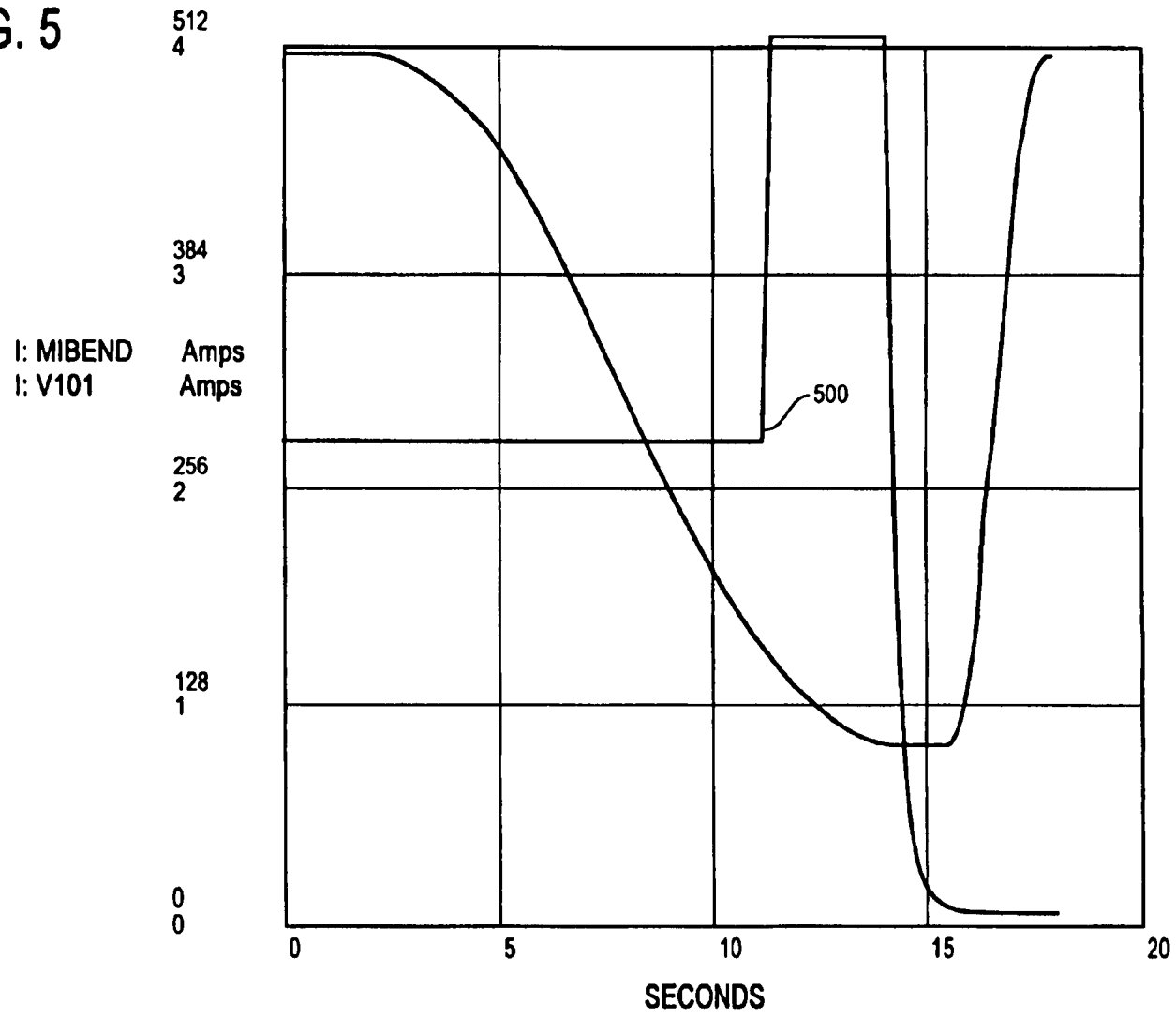
FIG. 5 is dipole corrector power supply system output electrical current (I:V101) vs. time.

The dipole corrector power supplies are similarly controlled by a computer control system. As shown in FIG. 4, the hardware implementing the trajectory control as a function of time and beam momentum had its table entries changed in order to include a separate term using the h01 table that supported deceleration corrections. The I:V101 curve in FIG. 5 shows the implementation of a dipole corrector electrical current change (the curve initially unchanged with the passage of time) during deceleration.

Another challenging synchrotron modification for implementing the unforeseen deceleration of hadron beams is in a radio frequency acceleration system. According to relativity, the higher the momentum of any object, the closer its velocity approaches the speed of light. Because the beam needs to be accelerated every time it passes through the radio frequency acceleration system, the beam needs to see the same portion of the electromagnetic field generated by that system each turn. This characteristic frequency of the electromagnetic field is—an integer multiple of the revolution frequency of the beam around the synchrotron. For example, in the above case of the Fermilab Main Injector the characteristic electromagnetic field frequency difference between the injection and maximum momenta is 0.3 MHz, compared to the characteristic field frequency of 53 MHz. This relatively small change in frequency is anticipated in the design of the cavities within which these electromagnetic fields are generated, and is accommodated by changes in cavity geometry or the addition of passive coils and antenna to modify the cavity characteristics to track this frequency change. These accommodating changes are analogous to changing the length of a trombone in order to support differing resonant tones in the musical instrument.

The shape of the dependence of hadron beam velocity on momentum is highly nonlinear, with very small velocity changes occurring at high momentum and relatively large velocity changes for momenta corresponding to velocitys less than 90% of the speed of light. For example, FIG. 2 shows that during the deceleration of a proton beam in the Fermilab Main Injector from the injection momentum (I:MMPRQ) of 8.9 GeV/c down to 2.0 GeV/c, the radio frequency acceleration system frequency (I:VDSPFO) was changed by 4.7 MHz, a factor of 15 times bigger change than the system design, and in the opposite direction!

In one embodiment of this invention, the computer control system and the radio frequency acceleration system are modified to enable the generation of electromagnetic frequencies below the injection frequency. The issue is then reduced to modifying the response of the associated cavities to produce a sufficient electromagnetic field strength inside the cavity. In the specific embodiment shown in FIG. 3, the lower fuzzy signals are the electromagnetic field strength inside the cavity during the decelerating of the hadron beam when no modifications are made to the cavities whatsoever, but the power levels from the radio frequency amplifiers generating this field was dramatically increased as the electromagnetic field frequency was changed by more than the cavity was designed to accommodate. The two different means of measuring the field strength (I:H28 SUM and I:H28 F0) both indicate it is possible to operate radio frequency acceleration systems in such a mode. The alterations to the radio frequency acceleration system and this result are believed to be so unobvious and contrary to usual approaches of practitioners in the field, and warranted publication of the deceleration results shown in FIG. 8 in the scientific literature.

Figure 14:
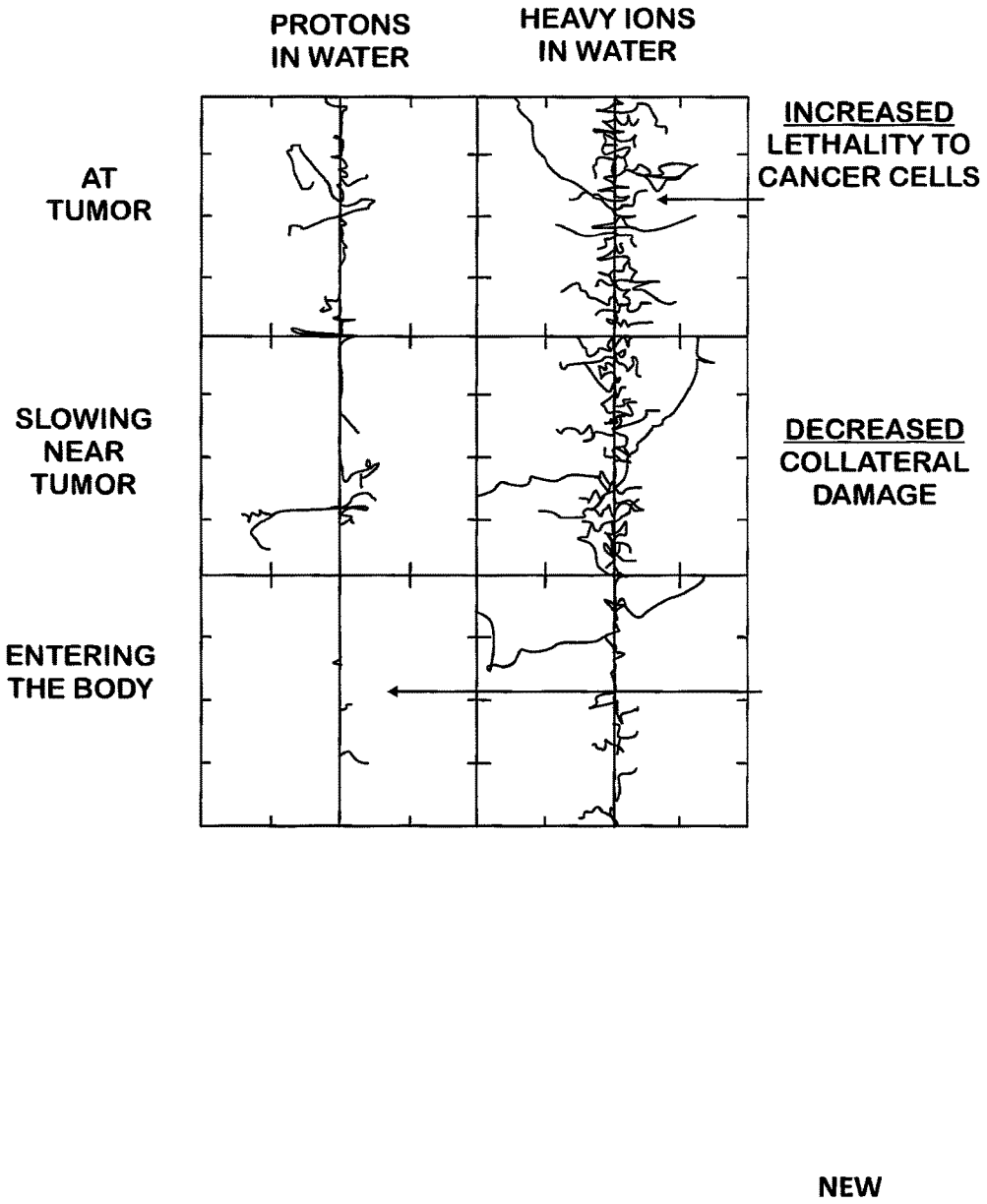
*FIG. 14, which is incorporated by reference from Ser. No. 60/316,711, filed Aug. 30, 2001, is a chart showing ionization tracks of protons and heavy ions in water.*

*FIG. 14 shows ionization tracks for protons in water and heavy ions in water, at a tumor, slowing hear the tumor, and entering the body. FIG. 14 also shows increased lethality to cancer cells and decreased collateral damage.*

*According to one aspect of embodiments of the present invention, a method decelerates antiprotons. The method comprises providing antiprotons to a particle accelerator ring. The antiprotons have a first momentum distribution with a first average momentum. The method further comprises operating the particle accelerator ring so as to apply electromagnetic fields to the antiprotons as the antiprotons travel around the ring. The method further comprises selectively applying the electromagnetic fields to the antiprotons as the antiprotons travel around the ring, such that the antiprotons have a second momentum distribution with a second average momentum less than the first average momentum.*

*Antiproton irradiation has utility in a variety of fields, including the treatment of cancerous tissue and the generation of radioisotopes within the body which are useful for imaging techniques and therapeutic treatment.*

*Currently, antiprotons are generated and used in experimental studies of elementary particles physics. These experiments are typically performed at large particle accelerators, such as the Tevatron at Fermi National Laboratory. The Tevatron includes various components which are designed to generate antiprotons, to accelerate these antiprotons to very high energies and momenta (typically to 1 TeV), and to collide these antiprotons together with other particles, such as protons. The results of the collisions can be analyzed to provide information regarding the physics of these and other elementary particles.*

*While these experimental studies of elementary particle physics require antiprotons with very high energies and momenta, other uses of antiprotons, such as the medical uses mentioned above, require relatively small energies and momenta. If the existing sources of antiprotons at such accelerators are to be used as sources of antiprotons for these other fields, the antiprotons have to be decelerated (i.e., the energy and momentum of the antiprotons will have to be reduced). In addition, to provide antiprotons to locations which are off-site from the particle accelerators, the antiprotons have to be decelerated sufficiently to enable them to be trapped in a container and transported to other locations. Because antiprotons are annihilated upon contacting matter, significant development has been performed to develop adequate containers (e.g., Penning traps) for transporting antiprotons.*

*Embodiments of the present invention decelerate the antiprotons by operating existing particle accelerators, which were designed to accelerate the antiprotons, under conditions which actually reduce the energy and momentum of the antiprotons.*

*A method of decelerating antiprotons, the method comprising: providing antiprotons to a particle accelerator ring, the antiprotons having a first momentum distribution with a first average momentum; operating the particle accelerator ring so as to apply electromagnetic fields to the antiprotons as the antiprotons travel around the ring; and selectively applying the electromagnetic fields to the antiprotons as the antiprotons travel around the ring, such that the antiprotons have a second momentum distribution with a second average momentum less than the first average momentum.*

*A method for decelerating antiprotons includes providing antiprotons to a particle accelerator ring. The antiprotons have a first momentum distribution with a first average momentum. The method further includes operating the particle accelerator ring so as to apply electromagnetic fields to the antiprotons as the antiprotons travel around the ring. The method further includes selectively applying the electromagnetic fields to the antiprotons as the antiprotons travel around the ring, such that the antiprotons have a second momentum distribution with a second average momentum less than the first average momentum.*

*This invention relates to the field of the treatment of cancer and other diseases by using radiation. Specifically, it addresses the use of antiprotons to deliver the ionizing radiation to the body; the advantages of using antiprotons rather than x-rays, 10 gamma rays, electrons, protons, heavy ions, mesons, or any other particles; the method of delivering the radiation to the desired region of the body; methods of enhancing the energy deposition within the body; the production of antiprotons; the collection and storage of antiprotons; the transport of antiprotons; and the application of the therapy in centralized and dispersed facilities.*

*Radiation has been used to treat cancer and other diseases for many years. In general, radiation is used to kill cancer cells immediately or to damage cancer cells enough to prevent reproduction. The fundamental problems with all forms of conventional radiation therapy are the delivery of an adequate dose (micro-density of ionization) to the desired cells (localization) at the right time without damaging healthy surrounding tissue.*

*With conventional radiation therapies, delivery of a dose of radiation adequate to damage cancer cells within a tumor is balanced against the amount of collateral damage that that particular dose of radiation will cause to healthy tissue. The specific nature of the radiation determines what collateral damage is done to healthy tissue and also determines the number of treatments required to deliver a dose calculated to be sufficient to treat a tumor. Treatment planning typically involves detailed computer modeling for all incident forms of radiation. These exact calculational schemes are specific to a particular patient and treatment facility, but the mathematical principles underlying the calculations are generally applicable.*

*Localization, the deposition of ionizing radiation within the desired region of the body, is performed internally or externally. Radiation therapy performed internally can be administered by radiation implant or via radioimmunotherapy. The general term, brachytherapy, refers to the insertion of an implant containing radioactive material directly in the tumor. It requires both the invasive surgical insertion and surgical removal of the radioactive implant. It is limited in its ability to treat large tumors uniformly. Radioimmunotherapy is a radiation therapy that involves delivering radiation to the surface of a tumor via the use of monoclonal antibodies that are tagged with radioactive atoms. It is also limited in its ability to treat large tumors.*

*Radiation therapy performed externally uses different methods of localization depending on the nature of the radiation. Simple collimation using appropriate shielding is used to localize the radiation field in two dimensions. Controlling the depth distribution of the energy deposition depends on the specific nature of the radiation; whether it is electromagnetic, charged particle, or neutral particle. Again, the specific nature of the radiation also determines how well defined the localization can be and how much damage is done to adjacent and intervening healthy issue.*

*When the incident radiation is electromagnetic (e.g. x-rays), more ionizing radiation is produced near the surface than deeper within the body. Electromagnetic radiation, as opposed to charged particle radiation, always delivers some ionizing radiation at all depths in the body. Thus, localizing the depth distribution of ionizing radiation is inherently more difficult with electromagnetic radiation than with charged particle radiation. Complex methods for the enhancement of the three dimensional localization of ionization within the body are well developed. These methods involving the overlapping of intersecting radiation fields are known by such names as gamma knife, intensity modulated radiation therapy (IMRT), and dose sparing methods. All these techniques minimize the dose to healthy tissue by spreading out the entering dose over a large volume, but all of these techniques still lack a true capability for three-dimensional delivery.*

*When the incident radiation is in the form of high-energy charged particles, more energy is deposited at the end of range, that is, more energy is deposited just before the particle stops than when it enters the body. This is the Bragg peak effect and is the basis for localization in depth. The distance the charged particles travel in the body is approximately the same for all similar charged particles of the same energy. Higher energy particles travel further in the body than lower energy particles. Well developed techniques exist*

*for delivering different energy protons (positively charged particles) to various locations in the body using a fixed or variable energy accelerator, beam transport systems, variable thickness degraders, scanning systems, patient positioning, and methods for correlating ionizing enemy deposition with various methods of imaging the internal structures of the body. The choice of ionizing particle determines the density of ionization (dose to the tumor) versus position along the path of the particle.*

*Neutral particle therapy (neutron therapy) achieves localization with overlapping fields and or the use of pharmaceuticals containing an isotope that captures the neutron and subsequently decays into ionizing particles. This combined method known as boron neutron capture therapy (BNCT) requires the development of special boron containing pharmaceuticals preferentially absorbed by the cancerous tumor.*

*A second problem with all forms of radiation therapy is delivering the correct density of ionizing radiation to the individual cells to either destroy the cells immediately or damage them enough to induce programmed cell death. On the microscopic scale, there are significant differences in the density of ionization and the nature of the damage produced by the various forms of radiation. These differences are accounted for by the concepts of the radiation adsorbed dose (Rad) and the relative biological effect (RBE). Radiation oncologists use these known concepts to plan the treatments using photons, neutrons, protons, heavy ions, or other charged particles. A significant improvement over the state-of-the-art would be the ability to change the density of ionization depending on the location (low density in healthy tissue and high density in diseased tissue).*

*Another problem with all forms of radiation therapy is the timing of the radiation treatments. Because the cells have repair mechanisms, they are able to recover from sub-lethal doses of radiation. Cells have variable sensitivity to radiation depending on whether they are actively reproducing or are in the resting state. Radiation oncologists typically administer many sub-lethal doses of radiation delivered over several weeks to destroy all the diseased cells when they are most vulnerable to radiation and to allow the healthy cells to recover between irradiations. This fractionation of the treatment is a significant inconvenience to the patient and is a major cost factor. A significant improvement over the state-of-the-art would be the ability to deliver a single dose of radiation to a tumor that is capable of destroying resting cells (cells that are not in the process of dividing) as well as those which are actively 5 dividing.*

*BRIEF DESCRIPTION OF THE DRAWINGS*

*There is an early publication that discusses the possibility of using antiprotons for biomedical applications. (L. Gray and T. E. Kalogeropoulos, "Possible Biomedical Applications of Antiproton Beams: Focused Radiation Transfer." Radiation Research 97,246-252 (1984).) The paper specifically mentions the "focusing" of radiation due to heavily ionizing particles emitted from annihilation. The sharpness of radiation transfer combined with antiprotonic radiography is considered attractive for special applications. The paper mentions simultaneous viewing (imaging) and treatment of areas of interest. The paper correctly identifies "the emission of low velocity nuclear fragments from the annihilation" as "responsible for the high concentration of energy transfer at the stopping point."*

*The direct comparison of charged beams of ions such as protons, el2, and Ne20 is in error with respect to the ratio of ionization energy deposited inside a tumor to that deposited outside a tumor versus the mass of the incident beam. The paper contains a figure comparing proton, heavy ion, and antiproton ratios of energy deposited inside a tumor, to that deposited outside the tumor for various size tumors below the surface. The figure appears to be conceptually correct. The paper does not discuss the concepts of the differing density of ionization for heavy ions versus protons or antiprotons, the relative biological effect, or the concept of reducing the fractionation of treatment required in the use of conventional radiation therapy. The only tumors specifically mentioned in the paper are pituitary and ocular.*

*The lack of any discussion of possible methods of implementation, the lack of details regarding the differing biological effect for antiproton annihilation products and heavy ions, and the lack of any mention of reduced need for fractionation of dose delivery demonstrate that the combination of ideas involved in this patent disclosure has not been previously disclosed in this paper.*

*A subsequent publication (T. E. Kalogeropoulos and R. Muratore, "Antiprotons for Imaging and Therapy" Nuclear Instruments and Methods in Physics Research B40/41 (1989) 1322-1325), discusses the use of antiprotons for stereographic imaging. It only mentions the possibility of maximizing radiation to a tumor and minimizing radiation delivered to tissues outside the tumor. There is no specific mention of methods of implementation or detailed discussion of the advantages.*

*A later publication (R. A. Lewis, G. A. Smith, and S. D. Howe, "Antiproton Portable Traps and Medical Applications", Hyperfine Interactions (1997) 109) describes some advantages of antiproton therapy over proton therapy in the enhanced energy deposition at end of range and in the value of external pion detection for imaging of the stopping point of the antiproton beam.*

*A relative biological dose was estimated, but was acknowledged to be an underestimation since "charged pions, gamma rays, and nuclear fragments also deposit energy into the tumor." Also described is the fact that certain features would enhance accurate placement of dose. The concept of precise deposition of high linear energy transfer radiation into breast tumor masses was proposed by S. D. Howe (Synergistic Technologies) in a 1997 response to a Department of Defense Small Business Innovation Research request for proposals.*

*The disclosed method comprises a new method of delivering heavy ion irradiation to a localized region of the body for therapeutic purposes. The means to do this involves the production, deceleration, storage, acceleration, transport, and delivery of a beam of antiprotons to the desired region of the body. After delivery, upon stopping in the body, the antiprotons undergo nuclear reactions with atomic nuclei in the body. Because of these nuclear reactions, energetic heavy ions with the optimum total energy are created and delivered at the desired location within the body producing the correct density of ionization and therapeutic effects. The conversion of relatively low density ionizing particles of variable energy on entry (the antiprotons) to high density ionizing particles (the heavy ion recoils) at the end of range is a process that occurs naturally.*

*This new method of delivering heavy ion irradiation also has the added benefit of real-time imaging to confirm correct localization of the therapy within a patient. This disclosure addresses the applications and means of implementing the use of antiprotons for therapy.*

*Details of the Method*

*The particular and preferred embodiments and implementations of technologies related to production, deceleration, storage, acceleration, transport, and delivery of antiprotons to the creation and delivery of heavy ions within the body for therapeutic purposes depend on optimization of engineering choices. Several ways of assembling a working system are outlined below.*

*The production of antiprotons is routinely performed at large accelerator facilities such as Fermi National Accelerator Laboratory. The antiprotons are produced at velocities close to the speed of light and are accumulated in a storage ring where the spread in velocities is reduced and the velocity is adjusted by deceleration to an appropriate velocity to prepare for further deceleration. If the antiprotons are to be used immediately, the deceleration is halted at the required energy and the beam of antiprotons is transported to the patient via a beamline. Variable energies of antiprotons can be delivered in a single sitting to a single patient so that the range of the antiprotons within the body will be sufficient to reach all parts of the tumor.*

*An alternate implementation consists of continued deceleration of the antiprotons to almost zero velocity (<20 keV) for long-term storage in a portable magnetic trap such as a Penning trap. Long-term accumulation and storage of significant numbers of antiprotons (>10e8) can be performed in a portable device consisting of an arrangement of magnetic and electrostatic fields known as a Penning trap or variation of it. The antiprotons stored in a trap are not useful for immediate therapy, but they can be transported to another physical location for acceleration and use.*

*The Penning trap implementation for therapeutic delivery of antiprotons comprises using the trap as an ion source for an accelerator such as a linear accelerator, a cyclotron, or a synchrotron. The accelerator can be either of fixed or variable energy. The preferred implementation is a variable energy accelerator capable of increasing the energy of the antiprotons such that their ranges in the body are sufficient to reach all parts of the tumor within the body. The fixed energy implementation comprises accelerating the antiprotons to an energy greater than that required to reach the tumor and then using a variable thickness degrader to adjust the energy and range appropriately. This second method requires the fabrication of multiple specialized boluses (typically fabricated from paraffin or polyethylene) for each patient.*

*The accelerator, beam transport, and beam handling systems are preferably modifications and extensions of existing technology, but newer technologies may be used as well. Except for the ion source, the accelerator, beam transport, and beam handling systems for antiprotons are essentially the same as for protons. Antiprotons have the opposite charge from protons, which means that reversing the magnetic and electric fields will produce the same behavior for antiprotons as for protons. A normal RF, sputter, or duoplasmatron ion source for protons could be replaced with a Penning Trap (a Penning Trap is described in the U.S. Pat. Nos. 5,977,554 and 6,160,263.).*

*Implementation of the method under either implementation scenario requires the calculation of the incident energy of the antiprotons to reach the various parts of the tumor. The energy depends on the total path length and the composition and density of the intervening healthy tissue. The methods for performing such calculations are well understood, but limited in accuracy by the prior knowledge of exact composition and densities of all intervening materials along the antiproton path. The exact overlap of the heavy ion irradiated volume with the tumor can be confirmed in real time by using position sensitive detectors for the pi mesons and/or gamma rays which result from annihilation to reconstruct the location of the annihilation radiation, i.e., the spatial location of the point of creation of the heavy ion. An alternative implementation of this idea is to use Positron Emission Tomography (PET) or Single Positron Emission Computed Tomography (SPECT) imaging to locate the position of the short-lived positron emitting isotopes created at the point of annihilation in real time.*

*The dose calculation methods used for x-ray, proton, or heavy ion therapy are not adequate for antiproton therapy outlined in this disclosure. The total radiation dose to various locations in the body and the resulting biological effects depend on the energy of the antiproton as it slows down in the body before annihilation and the dense ionization from the heavy ions produced subsequently. The motions of the antiprotons on entry produce a relatively low density of ionization and a biological effect that is the same or very similar to that of protons. The energetic heavy ions created within the body have very short ranges and produce dense ionization with a much greater biological effect relative to protons. The calculations needed for treatment planning will take into account the differences in the primary radiations (antiprotons and heavy ions) and their differing biological effects. The new combination of high-density ionization, (with heavy ions and the potential to kill resting cells with a single irradiation), and low-density ionization on entry (antiproton irradiation) is the basis for antiproton therapy. The detailed treatment protocols are patient specific, but the basic requirements are the same in almost all cases:*

1) *Create uniform, localized damage to the tumor sufficient to induce immediate or programmed cell death.*
2) *Minimize the incident radiation to healthy tissue and reduction of the total body dose to minimize the side effects to the patient.*
3) *Avoid severe inflammatory or necrotic tissue response*
4) *Eliminate or minimize the need for fractionated dose delivery.*

*These requirements place severe constraints on the absolute accuracy of dose localization, dose delivery, and dosimetry at all locations within the tumor.*

*Dosimetry, the measurement of the integrated radiation dose at each location in the body, can be obtained in several different ways. One possible implementation involves measuring the number of incident particles using an induction pick-off or a thin transmission detector. Such implementations are well understood and operate on the same principles as those used at a proton or heavy ion irradiation facility. A second possible implementation is to measure the total incident dose by detecting the mesons and/or gamma rays produced on annihilation of the incident antiprotons. This is also a real-time measurement that can be tied back to the beam rastering and/or beam blanking for precise dosimetry control of individual voxels. A third possible implementation is to measure the short-lived positron emitting isotopes produced at the time of incident antiproton annihilation. This third implementation is not performed in real time and is not amenable to active beam control during irradiation.*

*The methods for positioning the patient and the beam are the same or similar to those used for proton or heavy ion therapy. These methods include horizontal positioning of the patient with either fixed or rotating gantry and fixed or scanned beam. An alternate method uses a horizontal fixed or scanned beam with the patient in a standing position on*

*a rotatable platform. Pulsed beam operation correlated to the patient's breathing is preferable for all possible implementations.*

*The correlation and calibration of the beam delivery system with the imaging of the tumor can be implemented with either fixed or moveable imaging detectors and the use of appropriate phantoms. Antiproton therapy has the added benefit of real-time imaging to confirm correct localization of the therapy within a patient. The possible combinations of imaging techniques include but are not limited to the following: moveable or fixed MRI, CT, PET, or SPECT imaging of the tumor with fixed or moveable PET or SPECT detectors for imaging the delivered dose or fixed or moveable meson detectors for reconstruction of the annihilation vertices.*

*Antiproton Therapy offers significant advantages when compared to both surgery and traditional radiation therapies in the treatment of certain cancers. Antiproton Therapy offers the targeting advantages of the most technically advanced beam therapies associated with the immense benefits of increased lethality to cancer cells, decreased damaged to healthy, adjacent tissue, and the ability to kill cancerous tumors in 1-2 visits rather than the 30+ treatments required by other radiation treatment 30 regimes.*

*With regard to antiproton therapy, we have had several insights concerning the therapeutic effects of directing a beam of antiprotons onto a cancerous tumor. Seven of the most important of these insights are as follows:*

*Insight 1—In the irradiation process, antiprotons will behave very similarly to protons in that they can be targeted in three dimensions to be focused on a tumor, and that they cause very little collateral damage to healthy tissue as they enter a body.*

*Proton beam therapy is a commercially available treatment that is approved by the Food and Drug Administration (FDA) and is reimbursed by Medicare and many health-care plans. It will be possible to retrofit facilities currently used to deliver proton beam therapy to deliver antiprotons to patients.*

*Insight 2—In the irradiation process, antiprotons will behave very similarly to protons in that as they slow within a tumor, they will release the bulk of their energy in a localized end-of-range ionization zone, followed by a rapid decline in their dose energy. This is known as the "Bragg Peak" phenomenon. The Bragg Peak Phenomenon enables a delivery of a full, localized, and uniform dose of energy to the tumor.*

Figure 10:
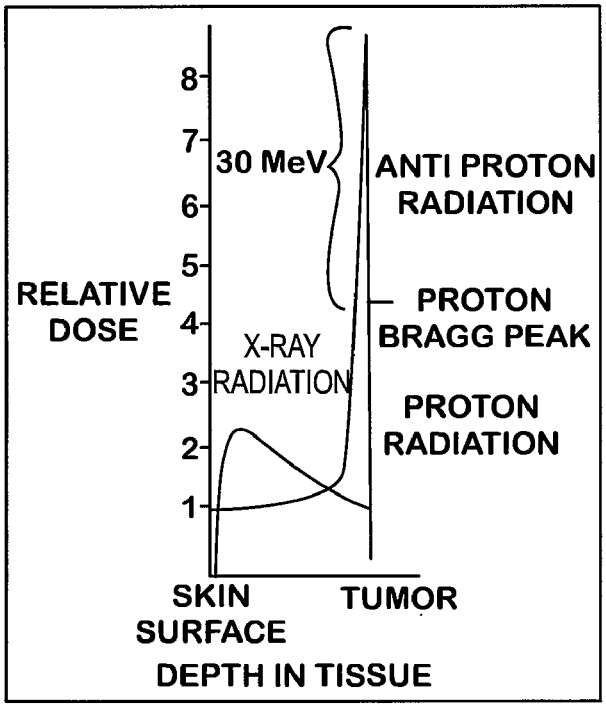
*FIG. 10, which is incorporated by reference from Ser. No. 60/316,711 filed Aug. 30, 2001, is a dose vs. depth curve for antiproton radiation, x-ray radiation, and proton radiation.*

*Insight 3—Antiprotons are very different from protons in that, after they slow and all of their kinetic is deposited into the tumor, they will then annihilate in the nucleus (on a neutron or a proton) of the nearest, largest atom, thus depositing an extra, very localized burst of cancer cell-killing energy in addition to what could be delivered by a proton. (See FIG. 10) This energy is in the form of the nucleus of the atom (a heavy ion), upon which the antiproton annihilation occurred, moving through tissue at high speed and destroying cancer cells in a very localized region (~30 microns or approximately the width of a cell). This extra burst of energy allows for the effective destruction of both "resting" cancer cells (i.e. cells that are not currently dividing) as well as "non-resting" cancer cells (cells that are in the process of dividing or replicating). Depending on the type of cancer, replication cycles vary from days to months. A cell is replicating, and therefore is the most vulnerable, only 1-7% of the time. The fact that this "replication cycle" exists, dictates the need for the 25-40 visits extending over many weeks being required for patients who are treated with traditional radiation therapy and chemotherapy. Antiproton Therapy thus eliminates the need for many multiples of doses of radiation therapy. This fact, in turn, means that antiproton therapy will not need the expensive delivery systems and complicated methods designed to ensure reproduceability of a three-dimensional dose profile over a great number of patient visits.*

Figure 11:
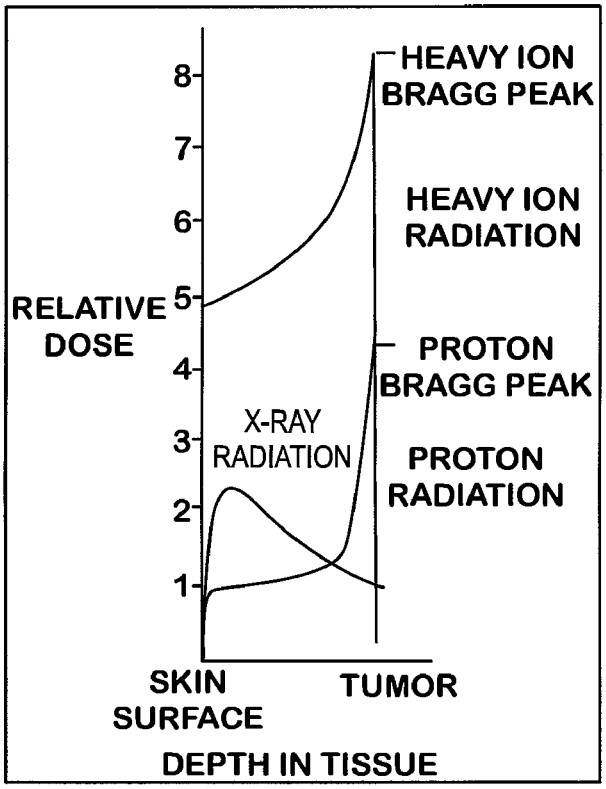
*FIG. 11, which is incorporated by reference from Ser. No. 60/316,711, filed Aug. 30, 2001, is a dose vs. depth curve for x-ray radiation, proton radiation, and heavy ion radiation.*

*Insight 4—In Antiproton Therapy, the annihilation event creates a heavy ion 5 within the tumor. Heavy ion therapy is a cancer therapy in that is under experimental development in Europe and Japan. Heavy ions cause more damage to a tumor than do protons, but dosing a patient with heavy ions causes significant damage to the healthy tissue between the surface of the body and the tumor. In some cases, heavy ions can cause as much damage to the healthy intervening tissue as do protons to the cancer cells. (See FIG. 11 for a comparison of heavy ion and proton therapies.)*

Figure 12:
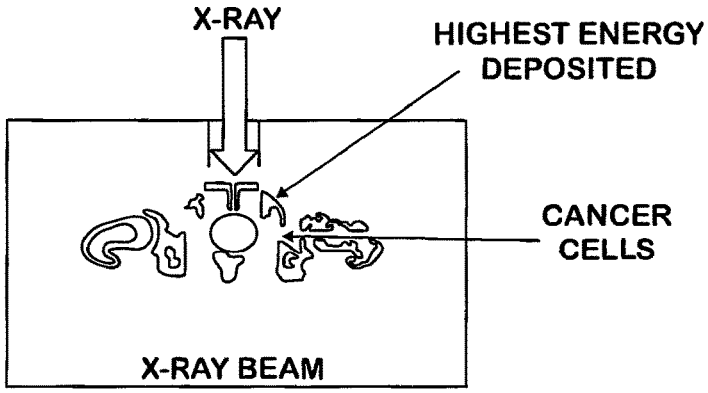
FIG. 12 PRIOR ART
*FIG. 12, which is incorporated by reference from Ser. No. 60/316,711, filed Aug. 30, 2001, is an image of a cross-section of tissue showing deposition of energy in tissue throughout its depth from incident x-ray radiation.*

*Insight 5—Antiproton therapy creates a heavy ion within a tumor, but it is very different than heavy ion beam therapy in that the surface of the body is not subjected to the high relative dose of heavy ions. Antiprotons thus exhibit the low entrance dose of protons coupled with the high cancer-killing energy transfer of heavy ions. The chart in FIG. 12 shows a comparison of ionization tracks of protons and heavy ions in water (humans are mostly water). Antiproton therapy offers the best of both worlds, having increased lethality to cancer cells with decreased collateral damage to healthy cells, shown in the shaded boxes. In addition, antiproton therapy offers an oncologist the ability to treat radiation-resistant cancer cells.*

*Insight 6—The particles formed by the annihilation event (pions and gamma rays) are useful species in that they could be used to image the tumor even as the treatment is taking place, using specialized detectors currently used in physics research applications. More attractively, when the antiproton annihilates on a neutron in a carbon, oxygen, or nitrogen atom, that annihilation event will create certain short-lived radioactive isotopes (lie, 150, 13N) within the tumor. These are exactly the same isotopes currently used to image patients with PET techniques. Accordingly, through antiproton therapy, these isotopes can be generated in situ as opposed to being delivered to the patient via injection of radiopharmaceutical compounds as is presently done for PET.*

*Insight 7—All infrastructure components for the most basic method for delivery of antiproton therapy now exist. Antiproton therapy can be delivered using methodologies very similar to those used for the delivery of proton beam therapy or it can be delivered with a much simplified and cheaper infrastructure. Alternatively, new systems and components may be developed and used for antiproton therapy.*

*Although several researchers have published articles (primarily in the 1980s) mentioning the feasibility of using antiprotons in the treatment of cancerous tumors, . . . scientists have connected these original feasibility observations with many new insights, including those noted above, to create a unique process for the treatment of cancerous tumors.*

*Comparative Advantages of the Preferred Method*

*Cancer is the second leading cause of death of Americans; nearly a million new cases of cancer are diagnosed just in the United States every year. Eighty percent of all cancers are diagnosed in persons aged 55 and older and so as the population of the United States ages, the prevalence of cancer is expected to rise. Current treatments are focused in three areas: surgery, radiation therapies, and chemotherapies. Forty three percent of all cancers can be effectively treated with surgery, eighteen percent of all cancers*

*can be effectively treated with radiation, and three percent of all cancers can be effectively treated with chemotherapy but the success factors are so low for individual treatments that combination treatments are used to treat the majority of cancers.*

*Antiproton therapy will replace common radiation treatments for many specific cancers and may replace surgery and chemotherapy in specific cases. Antiproton Therapy offers the ability to eliminate a tumor deep within a body without the trauma of surgery, without the collateral damage of many radiation therapies, and without the multiple treatments required by some beam therapies.*

*1. Advantages over Surgery*

*While surgery is used as a primary treatment in many cancers, cancer that can be cured with radical surgery must be in an early stage of development and must be localized. Radical surgery removes additional surrounding uninvolved healthy tissue in order to be able to ensure that the cancerous tissue is completely excised. Surgery for the removal of cancer is invasive and thus causes significant physical trauma to the patient. In addition, surgery must often be coupled with other harsh treatment methodologies, such as chemotherapy or radiation therapy in order to improve the patient's odds of being cured. In these cases, surgery is only the initial step in a regime.*

*Unlike surgery, antiproton therapy will cause no significant damage to the tissue in between the surface of the patient's skin and the tumor. Unlike surgery, antiproton therapy will be able to target the tumor in three dimensions so the destruction of local, uninvolved tissue will be minimized. Unlike surgery, antiproton therapy is noninvasive; the post-treatment process associated with antiproton therapy will not require the healing of a surgical incision. Infections associated with an incision will be eliminated; there will be no painful healing process.*

*2. Advantages over Chemotherapy*

*Chemotherapy is a common treatment for cancer—both those cancers that are localized and those that have metastasized throughout the body of the patient. Chemotherapy is essentially the controlled whole-body delivery of a substance that is toxic to dividing cells, thus chemotherapy kills both healthy and cancerous replicating cells throughout the body indiscriminately. Normal cells most likely to be affected are the blood cells that are forming in the bone marrow and cells in the mouth, digestive tract, reproductive system, and hair follicles. Chemotherapy drugs can also damage cells of the heart, kidneys, bladder, lungs, and nervous system. A chemotherapy regime is carefully chosen to target certain chemotherapy drugs against those cancer cells that are not resistant to those drugs.*

*As chemotherapy is typically effective only against replicating cells, it must be delivered to a patient in doses lasting over a period of many weeks. Patients may receive treatments daily, weekly, or monthly, and treatments are usually given in on and-off cycles that allow rest periods so that normal cells can be rebuilt and the patient can regain strength for the next dose of chemotherapy. While the most common short lived side affects are nausea, vomiting, hair loss, and fatigue, there are significant side effects that can last a lifetime, such as potential damage to bone marrow and permanent damage to the heart, lungs, kidneys and reproductive organs. Delayed side effects, such as a second cancer, may show up years later.*

*Unlike chemotherapy, antiproton therapy is a beam therapy that will be targeted in three dimensions and as such will impact only the cancerous tumor. As a targeted beam therapy, it will not cause damage either to the healthy cells in between the surface of the skin and the tumor or to the healthy cells surrounding the tumor.*

*Unlike chemotherapy, antiproton therapy is effective against resting cells (those cells that are not actively in the process of dividing). As it is effective against these resting cells in addition to those cells that are actively dividing, doses may be delivered over a period of one or more days rather than weeks or months. Antiproton therapy is effective against the cancer cells that it is targeted against—there will be no resistance to antiproton therapy.*

*With antiproton therapy, a patient will feel nothing during the treatment. Unlike chemotherapy, after an antiproton therapy treatment, patients will be able to continue their normal activities, with few or no side effects from the treatment. The patient will experience a much better quality of life during and after the antiproton therapy treatment than they will with chemotherapy treatments.*

*3. Advantages over Immunotherapy*

*Immunotherapy has been used as a treatment for cancer in various ways for a number of years but only recently has the concept of immunotherapy treatment been augmented by biotechnology research and development. Theoretically it is the perfect treatment; immunotherapy is aimed at mobilizing the body's own weapons (antibodies) to kill cancer cells. Immunotherapy uses drugs (for example, bacterial vaccines) to stimulate the production of antibodies. However, cancer cells can develop resistance to these antibodies. Recent developments in the biotechnology and genomic fields have been showing some progress in this treatment modality, but except for a very small number of cancer types and cases, immunotherapy is not a typical treatment. Radioimmunotherapy is a variation of immunotherapy where radiation is delivered to the surface of a tumor via the use of monoclonal antibodies (or other molecules) that are tagged with radioactive atoms. Both immunotherapy and radioimmunotherapy typically manage cancer rather than curing it.*

*Unlike immunotherapy or radioimmunotherapy, antiproton therapy is not limited to those cases where antibodies could potentially be stimulated to attack a cancerous growth. Antiproton therapy can be used against any type of tumor. Unlike immunotherapy or radioimmunotherapy, antiproton therapy treatments can be delivered in days rather than weeks and will be effective against the whole tumor. Antiproton therapy is always effective against the cancer cells that it is targeted against—there will be no resistance to antiproton therapy.*

*4. Advantages over Conventional Radiation Therapies*

*Conventional radiation therapy (x-ray) is a common technique to treat cancer and is used in hospitals all over the world. The surface of a body is exposed to x-rays in order to treat a tumor deep within the body. Radiation therapies generally cost more than chemotherapy, but are effective (i.e., exhibit high response rates) for many types of cancer. However, because radiation is not effective at killing non-replicating cancer cells, a lengthy, sustained schedule of treatments is required in order to target cells during their most vulnerable replicating state. The large doses that often are necessary to treat tumors also cannot be given at one time because of the severe side effects they would cause. On average, the course of treatment for radiation therapy takes 5 to 7 weeks. Typically, radiation oncologists try to avoid exposure of large parts of the body to radiation because this can cause serious side effects like a secondary cancer—one that develops after treatment for the initial cancer.*

*As with chemotherapy, there are cancer cells that are resistant to radiation, but the most serious shortcoming of X-ray radiation is that it can only be targeted in 2-20*

*dimensions. The picture in FIG. 12 (from the Lorna Linda University Medical Center web site, http://www.llu.edu/proton/) shows that the highest energy deposition from X-ray radiation is near the surface of the skin, and is not targeted onto the actual tumor cells. X-ray radiation can result in major side effects, including the shutdown or failure of normal body functions. X-ray radiation thus cannot be used near any sensitive organs such as the liver or kidneys.*

*Unlike conventional x-ray radiation therapy, antiproton therapy is effective against resting cells (those cells that are not actively in the process of dividing). As it is effective against these resting cells in addition to those cells that are actively dividing, doses may be delivered over a period of one or more days rather than weeks or months without the side effects that would be associated with a massive dose of x-ray radiation. Antiproton therapy can be targeted in three dimensions and so will both eliminate dose to healthy tissue and eliminate radiation-associated effects such as a secondary cancer. Antiproton therapy will be able to kill cancerous cells that are x-ray radiation resistant.*

*5. Advantages over Proton Beam Therapy*

Figure 13:
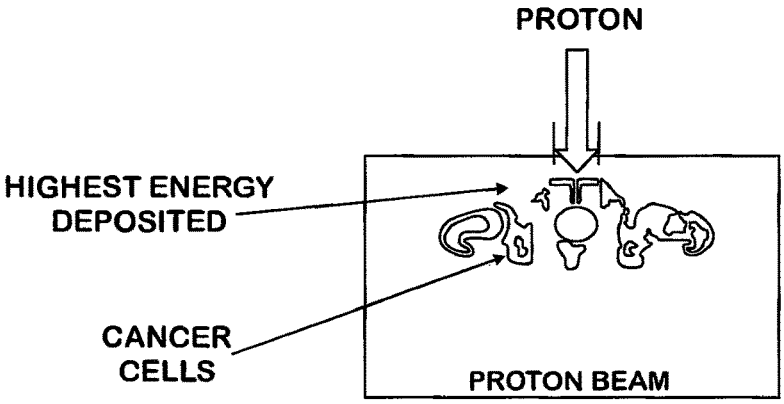
FIG. 13 PRIOR ART
*FIG. 13, which is incorporated by reference from Ser. No. 60/316,711, filed Aug. 30, 2001, is an image of a cross-section of tissue showing deposition of energy in tissue throughout its depth from incident proton radiation.*

*Proton beam therapy solves the problem of treating a tumor in two dimensions—it adds the third dimension by controlling radiation depth. Adjustment of the beam energy controls penetration depth. In proton beam therapy, beams of positively charged particles (protons) are directed at cancerous cells. Protons slow down as they interact with matter. As they slow within the tumor, protons release the bulk of their enemy in a localized end-of-range ionization zone, followed by a rapid decline in their dose energy. Virtually no radiation is expended beyond this point. This is known as the Bram Peak phenomenon (see Insight 2 above), and it enables a delivery of a full, localized, and uniform dose of energy to the tumor. As a consequence, very little radiation is deposited on peripheral tissue and collateral damage is minimized. Side effects are also thus fewer and milder than those experienced with chemotherapy or conventional radiation therapy. The picture in FIG. 13 (from the Lorna Linda University Medical Center web site, http://www.llu.edu/proton/) shows that the highest enemy deposition from proton beam therapy is targeted onto the actual tumor cells.*

*Proton beam therapy is not effective against resting cells and hence requires multiple treatments lust as chemotherapy and conventional radiation therapy. A rotating gantry system is used that is designed to emit charged particle beams from different angles to lower the potential of collateral damage from multiple treatments entering the patient at the same location. The patient is fitted with a body cast to insure precise positioning from treatment to treatment. These measures dramatically increase the cost of the therapies.*

*Like proton beam therapy, antiproton therapy can be targeted in three dimensions and causes minimal damage to peripheral tissue. Unlike proton beam therapy, antiproton therapy is effective against resting cells (those cells that are not actively in the process of dividing). As it is effective against these resting cells in addition to those cells that are actively dividing, antiproton therapy may be delivered over a period of days rather than weeks or months without the need for expensive delivery systems that are designed to deliver designed proton flux to specific locations in a patient over a period of several weeks.*

*6. Advantages over Heavy Ion Therapy*

*Heavy ion therapy is another beam therapy that has been gaining popularity worldwide. In this context, a heavy ion is an atom (e.g., a carbon atom) that has been stripped of its electrons. Like proton beam therapy, heavy ion therapy has the ability to deposit energy directly into the cancerous tumor in three dimensions and like proton beam therapy, heavy ions deposit most of their energy at their end of range (Bragg Peak phenomenon). Heavy ions deposit more energy into a tumor than do protons and hence have more cancer cell killing capability than do protons. Heavy ions do have the capability of killing resting cells, but while the killing power deposited on the tumor for ion therapy is dramatically greater, the collateral damage to healthy intervening tissue (that tissue between the skin surface and the tumor) is likewise greater—even greater collateral damage than for conventional radiation. The collateral damage for ion therapy can be even greater than the direct damage to the tumor with proton therapy. (see FIG. 11).*

*Like heavy ion therapy, antiproton therapy can be targeted in a three dimensional fashion directly onto a tumor, and like heavy ion therapy, antiproton therapy has the ability to kill resting cancer cells via a heavy ion mechanism. Unlike heavy ion therapy though, where the patient endures a direct dose of heavy ions to all tissue in between the surface of their skin and the tumor, the heavy ion in antiproton therapy is created within the tumor. Thus in antiproton therapy, the antiprotons enter the body depositing the low energies associated with single-charged, lightweight protons. At the tumor site, through the annihilation event, those antiprotons transform some of the atoms of the tumor into heavy, multiply-charged ions that are capable of killing resting cells in a very localized fashion.*

*7. Other Advantages of Antiproton Therapy*

*Pion Detection: Antiproton therapy has an additional advantage offered by the annihilation event. As an antiproton annihilates on a proton or a neutron of an atom within a tumor, other energetic particles are created in addition to the heavy ion. In particular, gamma rays and pions are emitted by this event. The direction and energy of the pions that exit a patient's body can be measured using a high-energy particle detector. In this way, the direction and the origin of the pions can be used to image where the annihilation event took place within the patient and can be used to determine the dose delivered to the tumor.*

*In Situ creation of PET Isotopes: PET is used to perform early detection of cancer, to monitor brain activity in Alzheimer's patients, and to and measure blood flow in heart disease cases. The particular short-lived radioactive isotopes used in PET ($^{11}C$, $^{15}O$, $^{13}N$) are currently delivered to patients via injection of radiopharmaceutical compounds. The procedure is FDA-approved and is widely accepted. In the employment of antiproton therapy, the annihilation event will create PET isotopes within the cancerous tumor, allowing for the real-time imaging of that tumor even as treatment is taking place.*

*Disclosed are methods relating to the field of the treatment of cancer and other diseases by using radiation. Specifically, it addresses the use of antiprotons to deliver the ionizing radiation and heavy particles to cancerous tissues, as well as the advantages of using antiprotons rather than x-rays, gamma rays, electrons, protons, heavy ions, mesons, or any other particles, as well as methods of delivering the radiation to the desired region of the body. In preferred embodiments, the incident antiprotons are used to destroy the cancerous cells and also to generate, in situ, PET isotopes, gamma rays and pi mesons which may be used to create real-time images the treatment site during treatment.*

*This invention relates to the field of the treatment of cancer and other diseases by using radiation. Specifically, it addresses methods of investigating the use of antiprotons in clinical radiotherapy.*

*Radiation has been used to treat cancer and other diseases for many years. In general, radiation is used to kill cancer cells immediately or to damage cancer cells enough to prevent reproduction. The fundamental problems with all forms of conventional radiation therapy are the delivery of an adequate dose (micro-density of ionization) to the desired cells (localization) at the right time without damaging healthy surrounding tissue.*

*With conventional radiation therapies, delivery of a dose of radiation adequate to damage cancer cells within a tumor is balanced against the amount of collateral damage that that particular dose of radiation will cause to healthy tissue. The specific nature of the radiation determines what collateral damage is done to healthy tissue and also determines the number of treatments required to deliver a dose calculated to be sufficient to treat a tumor. Treatment planning typically involves detailed computer modeling for all incident forms of radiation. These exact calculational schemes are specific to a particular patient and treatment facility, but the mathematical principles underlying the calculations are generally applicable.*

*Localization, the deposition of ionizing radiation within the desired region of the body, is performed internally or externally. Radiation therapy performed internally can be administered by radiation implant or via radioimmunotherapy. The general term, brachytherapy, refers to the insertion of an implant containing radioactive material directly in the tumor. It requires both the invasive surgical insertion and surgical removal of the radioactive implant. It is limited in its ability to treat large tumors uniformly. Radioimmunotherapy is a radiation therapy that involves delivering radiation to the surface of a tumor via the use of monoclonal antibodies that are tagged with radioactive atoms. It is also limited in its ability to treat large tumors.*

*Radiation therapy performed externally uses different methods of localization depending on the nature of the radiation. Simple collimation using appropriate shielding is used to localize the radiation field in two dimensions. Controlling the depth distribution of the energy deposition depends on the specific nature of the radiation; whether it is electromagnetic, charged particle, or neutral particle. Again, the specific nature of the radiation also determines how well defined the localization can be and how much damage is done to adjacent and intervening healthy tissue.*

*When the incident radiation is electromagnetic (e.g., x-rays), more ionizing radiation is produced near the surface than deeper within the body. Electromagnetic radiation, as opposed to charged particle radiation, always delivers some ionizing radiation at all depths in the body. Thus, localizing the depth distribution of ionizing radiation is inherently more difficult with electromagnetic radiation than with charged particle radiation. Complex methods for the enhancement of the three dimensional localization of ionization within the body are well developed. These methods involving the overlapping of intersecting radiation fields are known by such names as gamma knife, intensity modulated radiation therapy (IMRT), and dose sparing methods. All these techniques minimize the dose to healthy tissue by spreading out the entering dose over a large volume, but all of these techniques still lack a true capability for three-dimensional delivery.*

*When the incident radiation is in the form of high-energy charged particles, more energy is deposited at the end of range, that is, more energy is deposited just before the particle stops than when it enters the body. This is the Bragg peak effect and is the basis for localization in depth. The distance the charged particles travel in the body is approximately the same for all similar charged particles of the same energy. Higher energy particles travel further in the body than lower energy particles. Well-developed techniques exist for delivering different energy protons (positively charged particles) to various locations in the body using a fixed or variable energy accelerator, beam transport systems, variable thickness degraders, scanning systems, patient positioning, and methods for correlating ionizing energy deposition with various methods of imaging the internal structures of the body. The choice of ionizing particle determines the density of ionization (dose to the tumor) versus position along the path of the particle.*

*Neutral particle therapy (neutron therapy) achieves localization with overlapping fields and/or the use of pharmaceuticals containing an isotope that captures the neutron and subsequently decays into ionizing particles. This combined method known as boron neutron capture therapy (BNCT) requires the development of special boron containing pharmaceuticals preferentially absorbed by the cancerous tumor.*

*A second problem with all forms of radiation therapy is delivering the correct density of ionizing radiation to the individual cells to either destroy the cells immediately or damage them enough to induce programmed cell death. On the microscopic scale, there are significant differences in the density of ionization and the nature of the damage produced by the various forms of radiation. These differences are accounted for by the concepts of the radiation adsorbed dose (Rad) and the relative biological effect (RBE). Radiation oncologists use these known concepts to plan the treatments using photons, neutrons, protons, heavy ions, or other charged particles. A significant improvement over the state-of-the-art would be the ability to change the density of ionization depending on the location (low density in healthy tissue and high density in diseased tissue).*

*Another problem with all forms of radiation therapy is the timing of the radiation treatments. Because the cells have repair mechanisms, they are able to recover from sublethal doses of radiation. Cells have variable sensitivity to radiation depending on whether they are actively reproducing or are in the resting state. Radiation oncologists typically administer many sub-lethal doses of radiation delivered over several weeks to destroy all the diseased cells when they are most vulnerable to radiation and to allow the healthy cells to recover between irradiations. This fractionation of the treatment is a significant inconvenience to the patient and is a major cost factor. A significant improvement over the state-of-the-art would be the ability to deliver a single dose of radiation to a tumor that is capable of destroying resting cells (cells that are not in the process of dividing) as well as those which are actively dividing.*

DETAILED DESCRIPTION OF THE PREFERRED EMBODIMENT

*We have begun an investigation into the potential use of antiproton beams in clinical radiotherapy. Observed experimentally for the first time in 1955, antiprotons are the antimatter counterpart to protons, with a negative charge and parity and rest mass of 938 MeV/c2. Antiprotons have depth dose characteristics similar to protons in that they exhibit an energy dependent Bragg peak. The matter-antimatter annihilation event at the end of range is accompanied by the release of nearly 2 GeV, primarily in the form of energetic pimesons, but also neutrons, K-mesons and gammas, and of particular interest for therapeutic applications, charged nuclear fragments. Characteristics of antiprotons*

*and methods for using antiprotons for treatment of cancer and. other diseases are discussed in more detail in Applicant's U.S. Provisional Application No. 60/316,711, filed on Aug. 30, 2001, entitled NON-INVASIVE METHOD OF CELLULAR TERMINATION USING ANTIPROTON REACTIONS, the entire disclosure of which is hereby incorporated by reference and made apart of this specification.*

*We are using the Extension of Monte Carlo N-Particle (MCNPX) code developed at Los Alamos National laboratory to evaluate the feasibility of clinical antiproton therapy and in the design of physical experiments. MCNPX combines the traditional Monte Carlo NParticle (MCNP) particles (neutrons, photons, and electrons) with the high-energy, multiparticle transport features of the Los Alamos High Energy Transport (LAHET) code package. The intermediate energy model in MCNPX simulates antiproton annihilation and accompanying secondary particle production. The de-excitation of the residual nucleus after proton-antiproton annihilation is modeled using the multistage pre-equilibrium model and multi-fragmentation of light nuclei is based upon the Fenni-Breakup model.*

*Monte Carlo calculations confirm that the annihilation event produces a significantly larger Bragg peak relative to a proton dose deposition curve. For 150 MeV incident antiprotons; the peak-to-plateau ratio is approximately twice that for protons of a similar energy. The antiproton peak-to-plateau advantage over protons increases as the incident energy is decreased. Perhaps more significantly, a further potential clinical advantage exists in the form of the high relative biological effectiveness (RBE) of the charged nuclear fragments produced in-situ at the end of range.*

*While gammas resulting from the prompt neutral pion decay have sufficient energy to exit a human, roughly half of the charged pions produced will contribute to a relatively isotropic background dose. Nevertheless, this background is inconsequential relative to the clear physical and biological advantages.*

*This invention relates generally to the field of treating cancer, diseases, or any other conditions by the use of antiprotons and, more specifically, to an ability to detect, through measurement of energy and/or position of nuclear particles generated as a result of the treatment process, both the location of radiation delivered and the dose of radiation delivered, in real time.*

*Radiation Therapy*

*Radiation has been used to treat cancer and other diseases for many years. In general, radiation is used to kill cancer cells immediately or to damage cancer cells enough to prevent reproduction. The fundamental problems with all forms of conventional radiation therapy are the delivery of an adequate dose (micro-density of ionization) to the desired cells (localization) at the right time without damaging healthy surrounding tissue. There are two separate concerns that the radiation therapy industry has been trying to solve to optimize conditions for safe delivery of radiation therapy: 1) ensuring proper location of the energy deposition in real time; 2) ensuring proper amount (dosimetry) of radiation at each location in real time.*

*Radiotherapy or radiation therapy is the use of penetrating beams of high-energy xrays or gamma rays or streams of particles to treat various diseases such as cancer. The goal of a radiotherapy treatment protocol is to use radiation kill abnormal or unwanted cells with as little damage as possible to the normal surrounding cells. In conventional radiotherapy treatments, medical equipment is used to deliver high energy radiation to tumorous tissue (or other tissue to be irradiated). The placement of the radiation must be accurately controlled to ensure that the tissue to be treated receives sufficient radiation (dose) to be destroyed and the damage to the surrounding and adjacent non-diseased tissue is minimized. Currently, patient absorption of radiation is simulated and modeled before a patient is treated.*

*The simulation and modeling for external radiation delivery typically relies on computational methods to attempt to ensure localization of radiation delivery for all incident forms of radiation. The exact computational schemes are specific to a particular patient, to a particular type of radiation, and to a particular treatment facility. They are based on physical patient data, known radiation penetration data, and the intensity of the radiation to be delivered to a particular point in a patient. The correct density of ionizing radiation must be delivered to the individual cells to either destroy them immediately or to damage them enough to induce programmed cell death. On the microscopic scale, there are significant differences in the density of ionization and the nature of the damage produced by the various forms of radiation. These differences are accounted for by the concepts of the radiation adsorbed dose (Rad) and the relative biological effect (RBE). Radiation oncologists use these known concepts to plan the treatments using photons, neutrons, protons, heavy ions, or other charged particles.*

*After the treatment is planned, additional simulations with a patient are typically conducted. These could involve special x-ray or Computer Aided Tomography images as well as the construction of immobilization devices that permit some uniformity of patient positioning throughout a course of treatments. Computers are used to calculate the planned locale and dose distribution of the radiation. Location is presumed by delivery of a beam of radiation to marked skin and dosimetry is presumed by calibration of the instrument that delivers radiation to a patient. Medical practitioners cannot independently verify accuracy of "either variable in real time (i.e. during a particular radiotherapy session).*

*Typically treatment regimes last between two and five weeks. This fractionation of radiation delivery allows for intervening irradiated tissue to recover and also provides some assurance that the area planned to be irradiated receives some measure of radiation over the many treatment sessions. During the course of treatment, new images of the area irradiated are required (such as x-ray port films). These are used to ascertain the correctness of the location delivery model for the treatment plan, but do not provide either location or dose delivery information on a real-time basis.*

*Techniques exist for delivering certain types of charged particles to specific locations in the body using a fixed or variable energy accelerator, beam transport systems, variable thickness degraders, scanning systems, patient positioning, and methods for correlating ionizing energy deposition with various methods of imaging the internal structures of the body. In many cases, the use of collimation equipment or the use of techniques involving the overlapping of intersecting radiation fields are required. There is a complete reliance on patient models to calculate the location of where the radiation should be delivered. None of these techniques allow for a health care professional to actually measure or detect in real time where radiation is being delivered within a patient. These techniques do not allow for the detection of dose delivered in real time.*

*Other external radiation techniques such as neutral particle therapy (neutron therapy) attempt to attain localization with overlapping fields and or the use of pharmaceuticals containing an isotope that captures the neutron and subse-*

*quently decays into ionizing particles. This combined method known as boron neutron capture therapy (BNCT) requires the development of special boron containing pharmaceuticals preferentially absorbed by the cancerous tumor. Again this technique also does not allow for a health care professional to actually measure or detect in real time where radiation is being delivered within a patient and does not provide any information regarding the actual dose delivered.*

*Localization, the deposition of ionizing radiation within the desired region of the body, can also be performed internally. Radiation therapy performed internally is administered by a radiation implant. The general term brachytherapy refers to the insertion of an implant containing radioactive material directly into the area to be treated. Use of this technique has the advantage of allowing a health care professional to know exactly where and how much radiation is being delivered, but requires both the invasive surgical insertion and surgical removal of the radioactive implant. Real time detection of the placement of the brachytherapy unit can carried out using fluoroscopic detection techniques.*

*A significant improvement over the state-of-the-art would be the ability to change the density of ionization (the dose delivered) depending on the location (low density in healthy tissue and high density in diseased tissue). This would require the ability to detect, in real time, both the location and the intensity of the radiation delivered at that particular time to a patient. Currently, there are no techniques that allow for the real time detection of dose delivered to a particular point within a patient.*

*The use of antiprotons for radiation therapy would, as a result of the antiproton annihilation event at a targeted site, generate characteristic particles at that target site. These characteristic particles would then be used to conduct real-time measurement of both the position and dose of radiation delivered to a target within a body. This would ensure both proper location of the energy deposition in real time and proper amount (dose) of radiation at each location in real time.*

*Positron Emission Tomography*

*In Positron Emission Tomography (PET), images of metabolic, biochemical, and functional activities in living tissue are produced. A patient is injected with a radiopharmaceutical (a pharmacologically active agent that is tagged with a positron emitting isotope such as $^{11}C$, $^{15}O$, and $^{13}N$) and the area of interest is then imaged with a special device that measures the gamma radiation from the radioactive decay of that isotope. As the radiopharmaceutical travels throughout a patient, the computers and series of gamma detectors that constitute a PET camera are programmed to differentiate between the background radiation created by the general dispersal of the radiopharmaceutical in a body and the radiation from the area targeted by the pharmacologically active carrier. Three-dimensional images are created by the programmed movement of the patient and the detector array.*

*Positron Emission Tomography (PET) is used to perform early detection of cancer, to monitor brain activity in Alzheimer's patients, and to and measure blood flow in heart disease cases. The procedure is Food and Drug Administration-approved for many applications and is widely accepted.*

*A limitation to PET is the requirement for the use of relatively short-lived radioisotopes. Facilities that offer PET imaging must be located near a particle accelerator that produces the radioisotopes or must be able to use those radioisotopes that can be shipped. There is a patent (U.S. Pat. No. 5,977,554) that claims a system to generate biomedically useful radioisotopes using antiprotons. The concept is also reviewed in the paper "Antiproton Portable Traps and Medical Applications" (R. A. Lewis, G. A. Smith, and S. D. Howe Hyperfine Interactions 109 (1997) 155-164). These biomedically useful radioisotopes would always be generated outside of the body of a patient and administered by injection for ultimate use in standard three-dimensional PET imaging.*

*The concept discussed in this document of using PET isotopes generated by an antiproton annihilation event to carry out an in situ imaging process is a completely different. In the employment of antiproton therapy, when the antiproton annihilates on a neutron in a carbon, oxygen, or nitrogen atom, that annihilation event will create certain short-lived radioactive isotopes ($^{11}C$, $^{15}O$, $^{13}N$) within a patient's body at the point of the annihilation event. While these are exactly the same isotopes currently used to image patients with Positron Emission Tomography (PET) techniques, they are currently delivered to the patient via injection of radiopharmaceutical compounds. There is no technique known that can create PET isotopes within a patient.*

*This creation and subsequent detection of the PET isotopes created as a result of the antiproton annihilation event will allow for real-time detection of the location of the antiproton beam delivery even as treatment is taking place. This will ensure proper location of beam delivery in real time and will help limit injury to normal, untargeted tissue by allowing medical practitioners the ability to change the dose of radiation delivered to a specific location even as a treatment is taking place.*

*Positionality and Dosimetry*

*The desire of medical practitioners to verify beam delivery is demonstrated by the complexity of some of the methods used to confirm, beam localization. Jose R. Alonso of Lawrence Berkeley National Laboratory reviewed in two papers ("Review of Ion Beam Therapy", Invited paper, presented at the 7th European Particle Accelerator Conference," Austria Center, Vienna, Austria, Jun. 26-30, 2000, and "Medical Applications of Nuclear Physics and Heavy-Ion Beams" Invited paper, presented at the 7th International Conference on Nucleus-Nucleus collisions, Palais de la Musique et des Congres, Strasbourg, France, Jul. 3-7, 2002) the use of radioactive beams for treatment verification that was pioneered at the Bevalac at Berkeley, Calif. At the Bevalac, external beams of $^{19}Ne^{+}$ (a positron emitter and potential PET isotope) have been produced and used to verify accuracy of treatment plans. At the Heavy Ion Medical Accelerator in Chiba Japan (RIMAC), researchers are using an external beam of $^{11}C^{+}$ (another positron emitter and a PET isotope) to treat patients. Intensities at the HIMAC are sufficient for both PET imaging and treatment.*

*At the Gesellschaft fur Schwerionerforschung mbH (GSI) in Darmstadt, Germany, PET imaging with $^{11}C$ has been fully integrated into their treatment protocols. The $^{11}C$ has essentially the same range as the $^{12}C$ used as the primary beam for the heavy ion beam treatment so that imaging the positron annihilation radiation from the $^{11}C$ gives a direct measure of the stopping point of the beam. This allows for verification that the beam has actually reached the planned treatment volume. At GSI, treatment plans are modified based on measurements conducted during early treatment delivery to ensure accurate overall treatments.*

*In both of these cases, the positron-emitting species is administered to a patient by means of impinging the beam of that particular radioisotope onto a patient. The positron emitting radioisotope can be used as the external treatment beam (as at HIMAC) or as a calibration to an external heavy ion beam (as at GSI). Antiprotons have also been proposed*

*as simulators for the delivery of charged particle beams. This external application was proposed by Kalogeropoulos and Muratore in their publication "Antiprotons for Imaging and Therapy" (Nuclear Instruments and Methods in Physics Research B40/41 (1989) 13221325)). This particular technique however, would require much more than the "few" antiprotons said to be needed by Kalogeropoulos.*

*Antiprotons have been proposed for therapy-independent imaging applications. Antiprotonic Stereography was proposed by Gray and Kalogeropoulos (IEEE Transactions on Nuclear Science, NS-29; 1051; 1982). This technique was reviewed by Kalogeropolous, et al in other publications (Nuclear Instruments and Methods in Physics Research B40/41 (1989) 1322-1325). Kalogeropoulos and Muratore proposed administering antiprotons to a tumor to obtain an image after which the tumor could be treated ("Antiprotons for Imaging and Therapy" Nuclear Instruments and Methods in Physics Research B40/41; 1989, 13221325).*

*The use of charged pions for the diagnosis of tumor development was proposed by R. A. Lewis, G. A. Smith and S. D. Howe in their publications "Antiproton Portable Traps and Medical Applications" (Hyperfine Interactions 109 (1997) 155-164).*

*With regard to the employment antiprotonic annihilation products to detect the endpoint of an antiproton beam used in treatment, Gray and Kalogeropoulos proposed simultaneous treatment and viewing via the use of energetic charged mesons in their paper "Possible Biomedical Applications of Antiproton Beams: Focused Radiation Transfer." Radiation Research 97, 246-252 (1984)). Again, this particular technique would require many more than the "few hundred" antiprotons said to be needed by Kalogeropoulos.*

*Kalogeropoulos, et al proposed use of the same charged pions in their paper "Biomedical Potential of Antiprotons" (RAND Workshop on Antimatter Science and Technology, eds. BW Augenstein, World Scientific Singapore, Oct. 6-9, 1987 p. 640). They mentioned that energetic gammas produced from neutral pions are in principle more accurate but that measurement errors for charged particles are smaller.*

*The present invention covers methods and systems for generating positron-emitting or other radioisotopes in a body through the administration of antiprotons to a target site. The proper administration of antiprotons to a target site results in a series of complex annihilation events in which characteristic particles are generated and released. The present invention uses certain characteristic particles, such as neutral pions, emitted by antiproton annihilation to conduct real-time measurement of both the position and dose of radiation delivered to a target within a body. This application incorporates by reference U.S. provisional patent application 60/316,711 "Noninvasive Method of Cellular Termination using Antiproton Reactions".*

*Determination of the point of annihilation in real time will allow for an immediate feedback of beam positioning throughout a patient's treatment regime, that can be used to improve, for example, beam targeting in an area of interest. Determination of the number of annihilations in real time will allow for immediate feedback on the dose delivered to a particular target at any point in time. Comparison of the beam endpoint position with any imaging data taken prior to an antiproton treatment regime will provide verification of the extent of the area treated and information for future treatment planning, including additional areas that need to be treated (targeting), and calculations of duration of treatment and number of antiprotons to be delivered (dosage).*

*The localization of the energy deposition within the body when using antiprotons places strict requirements on the accuracy of positioning the beam and the locating the region of annihilation. This patent directly addresses the methods of implementing position sensitive detectors, tomographic reconstruction, two dimensional and three dimensional image reconstruction, vertex reconstruction, and multiple overlapping imaging techniques for visualization of antiproton irradiation procedures in approximate real time. The information generated can be used for confirmation of planned location and dose of radiation during and immediately after application of said radiation.*

*In principle, each incident antiproton will produce one or more possible events that can be used to determine the location in physical space of the annihilation of the antiproton. In this description, an event consists of several pieces of information that are correlated in time and can be combined to determine the location of the annihilation of the incident antiproton. In the preferred embodiment of this patent, the event may consist of, but not be limited to one of the following: (1) known incident energy, direction, and position of the antiproton; pion production at the time of annihilation; measurement of the position and direction of one or more of the pions and or other decay products; (2) annihilation of an antiproton on a stable nucleus in the body resulting in creation of a PET (positron emission tomography) isotope; decay of the nucleus (including but not necessarily limited to $^{11}C$, $^{13}N$, or $^{15}O$) by emission of a positron; annihilation of the positron on an electron in the vicinity (~1-2 mm.) of the antiproton annihilation; detection of the positron annihilation by coincident back-to-back 511 keV gamma rays. In the case of event (1) above, the location of the annihilation would be determined by vertex reconstruction. In the case of event (2) above, normal tomographic image reconstruction would be implemented. Other possible implementations may include such technologies as, but not necessarily limited to, SPECT (single photon emission computed tomography) or combinations of the above.*

*The correlation of the reconstructed image with the pre-determined position for deposition of energy with antiprotons is also part of the preferred embodiment of the patent. The initial determination of the region to be irradiated can be made by one or more of several imaging technologies such as PET, MRI (magnetic resonance imaging), CAT (computer assisted tomography), or multiple x-ray projection. The first three methods mentioned above lend themselves to two and three dimensional reconstruction methods and virtual reality presentations. The overlap of such three dimensional images with the antiproton annihilation generated images described above can be accomplished in one or more ways such as immobilization in a reference cast and patient transfer, sequential imaging at the time of treatment with moveable detectors, or simultaneous imaging with multiple purpose detectors. Certification and calibration of the images and the overlap and correlation between images can be implemented with the use of known phantoms.*

*The preferred method of administering radiation with antiprotons consists of planning a particular treatment protocol based on the measured positions to be irradiated, the assumed compositions of the intervening materials, the distances to be traversed, and Monte Carlo simulations of the energy loss of the antiprotons on entering the body. The result of these calculations is a prediction of the three dimensional distribution of the end of range of the administered antiprotons. This preliminary simulation is a model calculation enabling an optimized treatment protocol to be planned. The important point to remember is that this treatment plan is only a best estimate. The result of this*

*calculation is no better than the assumptions on which it is based. There are many possible errors that can produce an incorrect prediction. Among the most important are incorrect assumed composition, incorrect assumed density, and incorrect knowledge of the stopping power of the incident antiprotons as a function of composition and energy. This patent specifically provides a method for correcting the accumulated errors in the model treatment plan at the time the radiation is delivered.*

*A possible implementation of the method is to deposit a known, small amount of antiproton radiation at one or more fixed positions within the tumor. The locations of the fixed antiproton deposits would be determined by either the vertex reconstruction mentioned above and or positron emission tomography as previously described. These antiproton-generated fiducials produced within the tumor by the beam are then compared to the initial model dependent treatment plan calculations. Any differences between the calculated and measured positions would be used immediately to correct the total errors in the model. This updated treatment plan would then be used or the process could be iterated until convergence to the desired accuracy is achieved. The ability to create the model, calculate the dose to be delivered, measure the delivered dose, modify of the model, and iterate the process to the desired degree of accuracy spans many different professions.*

*This process of detection of various characteristic particles generated as a result of the antiproton annihilation process will provide, in the course of therapy, simultaneous verification of both the location and dose of radiation delivered by antiprotons and thus will allow for modification and optimization of a treatment even as it is taking place. A medical practitioner can therefore choose whether to measure location, or dose, or both simultaneously.*

*Real-Time Beam Delivery Detection: Confirmation of Planned Location of Beam Delivery*

*The specific mechanism by which antiproton therapy would destroy any targeted tissue will also enable the detection of the location of the delivered antiproton in real time i.e. during the treatment of a patient. In the irradiation process, as antiprotons slow within the targeted tissue, they release the bulk of their kinetic energy in a localized end-of-range ionization zone. After they slow and all of their kinetic energy is deposited, they then annihilate in the nucleus (on a neutron or a proton) of the nearest, largest atom, thus depositing an extra, very localized burst of energy. When an antiproton annihilates at rest on a proton it produces a number of energetic pions, charged particles, and gamma rays. These pions, particles and gamma rays all move away radially from the annihilation site. It is possible to track these species, which all point back to a common point, to the vertex of the annihilation event. Locating the vertex allows for the removal of certain types of backgrounds and the reconstruction of the physics of the event, thereby allowing for the visualization of a distributed source of annihilation radiation.*

*Another attractive option is to use the particles generated from decay of any radioisotopes generated in-situ as a result of the antiproton annihilation event. For example, when the antiproton annihilates on a neutron in a carbon, oxygen, or nitrogen atom in a body, that annihilation event will create certain short-lived radioactive isotopes (e.g. $^{11}C$, $^{15}O$, $^{13}N$) at the point of annihilation. These particular isotopes are the same isotopes currently used to image patients with Positron Emission Tomography (PET) techniques. In the current usage of PET imaging, these isotopes are delivered to a patient via injection of a radiopharmaceutical compound and infiltration of that compound to a specific site within a body where they are used to image functionality of a particular organ or site. When they are generated in-situ by the impingement of antiprotons, they do not provide information on organ functionality, but they can be used to pinpoint the location of delivered antiprotons within a patient. This would allow for real time determination that the radiation delivered is on-target within a patient, using familiar techniques and equipment equivalent to those currently being used for PET, but in a different modality.*

*Real-Time Dosimetry: Confirmation of Planned Dosage Delivery*

*Dosimetry is the measurement of the number of antiprotons delivered in each location of the body and is an important part of any treatment protocol. The annihilation of an antiproton in living tissue creates a heavy ion that destroys that living tissue (cancerous tissue or any other targeted tissue) in a one or two cell radius. The annihilation event simultaneously produces several high-energy particles—pions and gamma rays—that enable the detection of the antiproton delivery in real time—i.e. during the treatment of a patient. The pions and prompt gamma rays can also be used to provide concurrent information on the dose of radiation being delivered, even as the treatment is taking place.*

*There are at least three possible ways to perform dosimetry: 1) count the number of incident particles by well known detection methods or integrate the incident charge; 2) measure the prompt radiation associated with the annihilation of the antiprotons; 3) measure the delayed activity induced by irradiation with antiprotons. The first two methods have the advantage of real time measurement for active control of the beam. The third method is based on positron activity and has the advantage of measuring the spatial uniformity and extent of the delivered dose in the body. When combined with the other imaging methods used for treatment planning, this third method is useful for confirming the actual received dose.*

*For methods 1 and 2, the number of gamma rays and pions that are detected outside of the body is directly proportional to the number of antiproton annihilations that have occurred inside the target volume and, therefore, the number is also directly proportional to the physical dose of radiation that has been delivered to the target volume. Accurate dosimetry requires coupling the image of the irradiated volume with the number of external particles that are detected, as dose is defined as the amount of energy delivered per unit mass of target irradiated. Given a knowledge of both the irradiated volume and the total number of annihilations that have occurred within the volume, one could determine the dose delivered to a patient as a treatment is taking place.*

*For method 3, the dose delivered could be measured by measuring the radioactive decay of any radioisotopes generated in-situ as a result of the antiproton annihilation event. Again, when the antiproton annihilates on a neutron in a carbon, oxygen, or nitrogen atom in a body, that annihilation event will create certain short-lived radioactive isotopes (e.g. $^{11}C$, $^{15}O$, $^{13}N$) at the point of annihilation. These particular isotopes are the same isotopes currently used to image patients with Positron Emission Tomography (PET) techniques. When they are generated in-situ by the impingement of antiprotons, they do not provide information on organ functionality, but they can be used to calculate the dose of delivered antiprotons within a patient. This would allow for a determination that the correct dose of antiproton therapy is being delivered to a patient during treatment,*

*using the familiar techniques and equipment equivalent to that currently being used for PET. Again, the data obtained from the PET instruments would be used in a different fashion than is known in the field today, and computational capabilities would have to be added in order to be able to compensate for the timing of the radioactive decay from the isotopes generated.*

*A preferred embodiment of the idea consists of a beam delivery system compatible with a high efficiency, high spatial resolution detector system in close proximity to the patient. The beam delivery system consists of either a fixed beam and moveable patient or a fixed patient and a moveable beam or a combination of the two. The moveable beam is implemented with magnetic and or electrostatic steering, techniques that are well understood.*

*In current radiation therapy techniques, the desired dose to be dispensed to a patient is calculated before delivery of the radiation. Simulations and calculations are done based on physical examinations, laboratory tests, and imaging studies. Information from the simulations and calculations is used to determine how much radiation is needed, how it is to be delivered, and the number of treatments required. Researchers are now testing various Monte Carlo simulations to clinically improve the accuracy of radiotherapy dose calculations. Dose distributions in experimental phantoms and in test patients are used to verify optimized treatment plans based on these Monte Carlo calculations.*

*The current radiation techniques thus treat a patient to deliver radiation as predicted by a model, but the model may not accurately portray the patient. Real time verification of radiation delivery (location and dose) will be able to validate a treatment plan even as a patient is being treated. Updates can take place during the delivery of therapeutic radiation.*

*Radiation overexposures are not unknown using current radiation therapy techniques. Overexposures of radiation therapy patients in Panama were attributed to lack of treatment plan verification and to the method of entering beam block data into radiation treatment planning software. Use of a radiation therapy procedure that provides real-time imaging and dose feedback would not allow these radiation overexposures.*

*The importance of a post-treatment verification system for dose and placement of radiation therapy is described in U.S. Pat. No. 5,394,542 "Verification System for Radiation Therapy". This patent provides for "a verification system that can be used in conjunction with a radiation intensity compensator to minimize the possibility of an uncontrolled beam ray irradiating nontumorous tissue. In one embodiment, the verification system may collect tomographic data on absorbed radiation within the patient and generate tomographic absorption images therefrom. These images may be used for radiation dose verification as well as for planning subsequent therapy sessions." Again, this technique is a post-radiation technique that does not provide real-time feedback on location or dose.*

*A substantial advantage of the PET image created using antiprotons as described above is that the signal-to-noise characteristic of the resulting image is much improved over standard Positron Emission Tomography images. This is due to the fact that essentially no background signal is produced using antiprotons to create the radioisotopes at the end-of range positions, whereas a lame background signal is produced in standard PET imaging due to incomplete selectivity of the infiltration process of diffusing the radioisotopes to the targeted regions of the body. Radioisotopes that don't migrate to the targeted regions will emit radiation that tends to obscure the desired PET image by creating an undesirable background of emitted intensity of radiation. The image created from the annihilation of antiprotons contains no such background as the radioisotopes that are created by antiproton annihilations are created only at the end-of-range positions within the target. The signal-to noise improvement using antiproton annihilations to create the positron-emitting radioisotopes would be perfect except that occasionally a few antiprotons of the incident beam of antiprotons will annihilate prematurely before reaching the targeted volume, due to direct nuclear collisions of the incident antiprotons with nuclei of intervening tissue in the body. The premature annihilation events are relatively rare and result in a low-intensity signal that illuminates the track of the incident path in the final PET image.*

*Another inventive aspect of the present invention is the use of the low-background characteristic of antiproton-produced radioisotopes coupled with the short half lives of the radioisotopes to image flow and/or diffusion characteristics within vessels or through tissue. Antiproton annihilations in blood or other fluids create short-lived radioisotopes within the blood or fluids. The most common radioisotopes that will be produced in human fluids are $^{11}C$, $^{15}O$, $^{13}N$, as these atoms are the most common atoms found in the body. These radioisotopes have half lives of 20, 10, and 2 minutes, respectively. Circulatory blockages or hemorrhages could be readily imaged using standard PET imaging equipment to follow the diffusion of small volumes of blood or fluid that is initially irradiated with a low-intensity, highly localized pulse of antiprotons. A low-intensity pulse of antiprotons creates a small volume of radioisotopes that will flow with the blood or fluid in the local region. The path of the flow is readily imaged from the emitted radiation because the background intensity is negligible, as described above, and the resulting signal-to-noise is high. The short half lives of the radioisotope species result in large signals relative to background levels for ease of detection and short total lifetimes for low residual effects.*

*When a pbar annihilates at rest on a proton it produces a number of energetic charged particles and gamma rays. These particles and gamma rays all move away radially from the annihilation site. It is possible to track these particles and gamma rays which all point back to a common point, the vertex. This is a common technique in high-energy physics to visualize the source of the radiation using vertex reconstruction. In high-energy physics, locating the vertex allows removing certain types of backgrounds and to reconstruct the physics of the event. The same can be used for visualization of a distributed source of annihilation radiation. It is described here a detector system that will allow visualizing on-line the distribution of annihilation sites produced using a pbar beam stopping in tissue.*

*In order to examine the detector design limitation a model is used. Assume a pbar beam penetrating and stopping at the center of a sphere of water 15 cm in radius. Assume the annihilation radiation is from the pbar-p annihilation of the proton in the hydrogen atom of the water molecule. The detector must be placed outside the sphere for the detection of the radiation products: electrons, muons, pions, kaons, and gamma rays. For this discussion, the annihilation of the pbar with an oxygen nucleus is ignored. (It would have in addition to the pions, kaons, and gamma-rays; protons, neutrons, ion fragments, and hard x-rays.)*

*The charged particles escaping the 15 cm will have energies greater than that given by the stopping range in 15 cm of H2O shown in table 1.*

TABLE 1

Kinetic energy and momenta for particles stopping in 15 cm H2O are shown.

| Muon | Pion | Kaon | Proton |
|---|---|---|---|
| 130 MeV/c<br>80 MeV | 160 MeV/c<br>92 MeV | 350 MeV/c<br>124 MeV | 540 MeV/c<br>155 MeV |

*The mean multiplicity of charged mesons from the annihilation site is 3, and for neutral mesons are 2. The fraction of purely neutral annihilations is 4%. The fraction of annihilations producing at least one neutral meson is >40%. The mean momenta of these mesons are about 400 MeV/c.*

TABLE 2

Mean decay distances and the dominant decay products of pbar-p annihilation are given.

| Particle | Muon | Charged pion | Neutral pion | Charged kaon | Neutral kaon short | Neutral kaon long |
|---|---|---|---|---|---|---|
| $c \cdot \tau \cdot$ (cm) | $6.586 \cdot 10^4$ | 780.3 | $2.5 \cdot 10^{-6}$ | 370.9 | 2.675 | 1554 |
| Major Decay products | evv | μv | γγ | $\pi \cdot \pi \cdot \pi$<br>$\pi \cdot \pi^0$ | $\pi \cdot \pi$<br>$\pi^0 \cdot \pi^0$ | $\pi^0 \cdot \pi^0 \cdot \pi^0$<br>$\pi \cdot \pi \cdot \pi^0$ |

*From tables 1 and 2 we see that the muons and charged pions mostly escape the 15 cm sphere. The neutral pion decays in less than 0.025 microns into a pair of gammas that escape with the energy carried by the pion. Only a fraction of the charged kaons escape the 15 cm sphere. The neutral k short decays within 2.65 cm from the primary vertex producing a secondary vertex away from the annihilation site. During the process of the charged particles traversing the 15 cm of H2O, they will multiple scatter causing direction changes and therefore impacting our ability to point back to the exact annihilation site. This change of direction is given by the following expression that depends upon the momentum of the particle; it's charge, and the material through which the particle is passing.*

$$\theta_0 = 13.6 \cdot \mathrm{MeV} \cdot \frac{z \cdot \sqrt{\frac{x}{X_0}} \cdot \left(1 + 0.038 \cdot \ln\left(\frac{x}{X_0}\right)\right)}{\beta \cdot c \cdot p}$$

*where*

*z is the charge of the particle*

*$X_0$ is radiation length of the material*

*p is the momentum of the particle in MeV/c*

*$\theta_0$ is the angle in radians*

Figure 15:
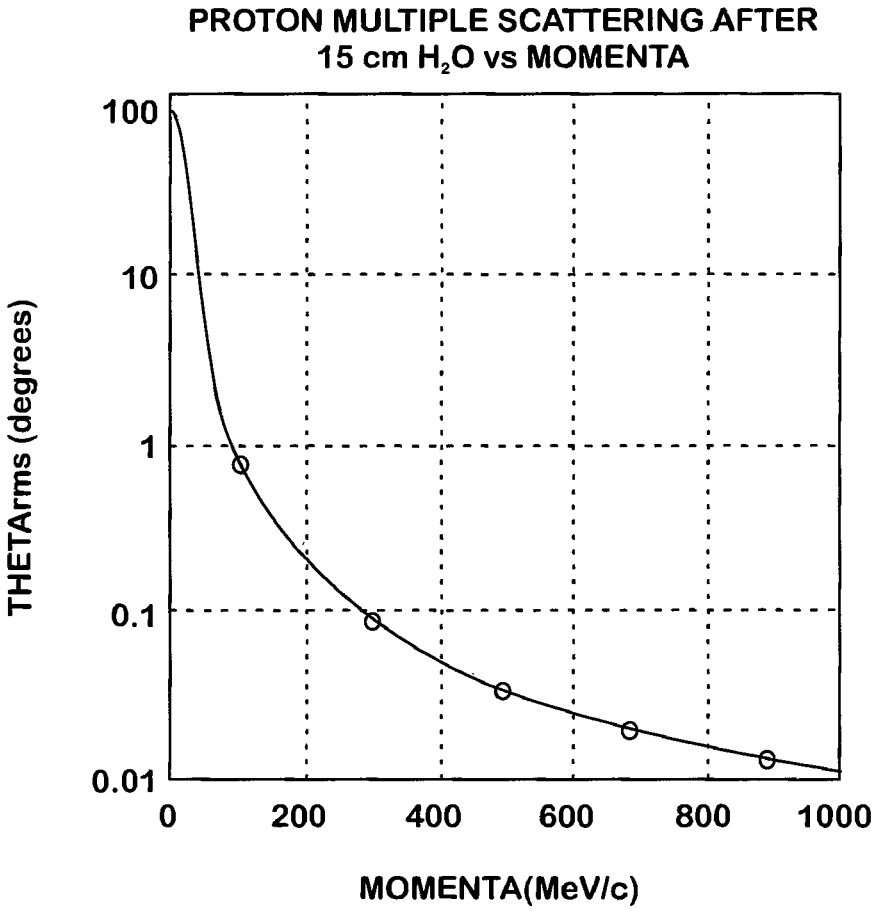
*FIG. 15, which is incorporated by reference from Ser. No. 60/388,428, filed Sep. 29, 2002, is a chart showing proton multiple scattering after 15 cm H2O vs. Momenta.*

*In fact, the pbar (540 MeV/c) will scatter laterally to the direction of the beam by an rms value of about 4 mm coming to the center of the sphere. See FIG. 15. Charged pions (160 MeV/c) just reaching the surface of the sphere will have scattered laterally to the direction of the track by an rms of about 7 mm. Charged pions having momenta less than 160 MeV/e stop in the water and are not detected. This limits how precisely we can point to the vertex using detection of the charged particles. See FIG. 16.*

*The pions with a momentum of 300 MeV/c will scatter laterally by an rms of 2.5 mm. The highest momentum of the pions would allow between 1.5 and 2.5 mm precision of locating the annihilation vertex. Charged kaons are worse. Of course, if the site of annihilation is closer to the surface one gains in precision (3× at 1.5 em).*

*Multiple scattering will be the limiting error for visualization of the geometry of annihilation sites. One cannot hope for better than 1.5 mm precision for viewing annihilation geometry located under 15 cm of H2O using charged pion tracking.*

*An alternative route to visualization would be to use the neutral pions. They decay to a pair of gammas sharing a total energy of 134.97 MeV plus the momentum of the neutral pion. The pair of gammas points back to the position at which the pion decayed. The gammas have a high probability of escaping the 15 em without interacting. The gamma rays can be detected in a high z, high-density media, where they interact creating an electromagnetic shower. The shower energy is contained (95%) inside a cylinder of radius 2×RM, the Moliere radius, and a length of about 20 XO radiation lengths.*

TABLE 3

Some physical properties of three selected materials used for shower detection are shown.

| Material | NaI(T1) | $PbWO_4$ | W |
|---|---|---|---|
| Radiation Length (cm) | 2.59 | 0.89 | 0.323 |
| Moliere Radius cm | 4.5 | 2.2 | 0.8 |
| dE/dx (MeV/cm) per mip | 4.8 | 13.0 | 24.0 |
| Decay time (ns) | 250 | 5-15 | — |
| Relative light output | 1. | 0.01 | — |

*In fact, the lateral distribution of the shower relative to the shower axis is quite peaked on the shower axis. Moliere has calculated this distribution. An analytical approximation to Moliere's calculation is given for r 1RM<1:*

$$\frac{dF}{dr} = 2.85 \cdot (1 + 4 \cdot r) e^{-4 \cdot (r)^{\frac{2}{3}}}$$

*where*

$$R_M = \left(\frac{E_s}{\varepsilon}\right) \cdot X_0,$$

*the Moliere radius*

*$X_0$ is the radiation length for the material*

*$E_s$=21 MeV*

*ϵ is the critical energy, 610 MeV/(Z+1.24), 8.1 MeV for W*

Figure 17:
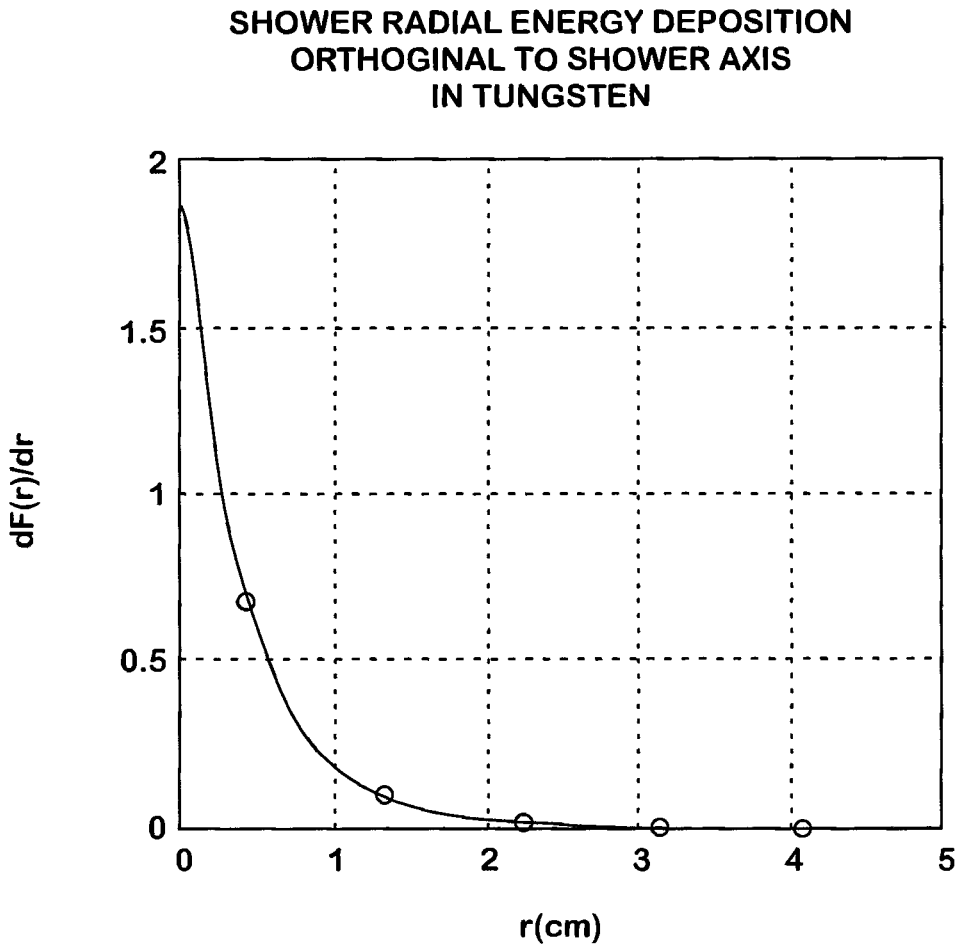
*FIG. 17, which is incorporated by reference from Ser. No. 60/388,428, filed Sep. 29, 2002, is a chart showing shower radial energy deposition orthogonal to shower axis in tungsten.*

*In FIG. 17, the radial distribution of energy relative to the shower axis for tungsten is shown. Another material having a similar Moliere radius and density is uranium. These materials are not actively sensitive to the shower and would require a sandwich type of construction using layers of tungsten and scintillator. The design has been employed before but not for the purpose of localizing the shower axis. Single points on the shower axis have been localized to about 1 mm using this idea.*

*We would want multiple points along the shower axis thus giving a vector pointing back to the vertex for each gamma (coming from pi zero decay). The mean number of gammas is four for each annihilation in pbar-p and can be as many*

*as 10. Thus, we should be able to take a cross over point to give the vertex point for the image.*

*The size of the sensing element for the shower is determined by the Moliere radius, 3.23 mm. Depending upon backgrounds and gamma multiplicity one would either use a 3.23×3.23×3.23 mm3 in a matrix or a crossed 3.23×3.23×200 mm3 hodoscope plastic scintillator array to sample the shower's charged particles passing between sandwich plates. One can aim for 500-micron precision in location of the vertex using this technique.*

Figure 18:
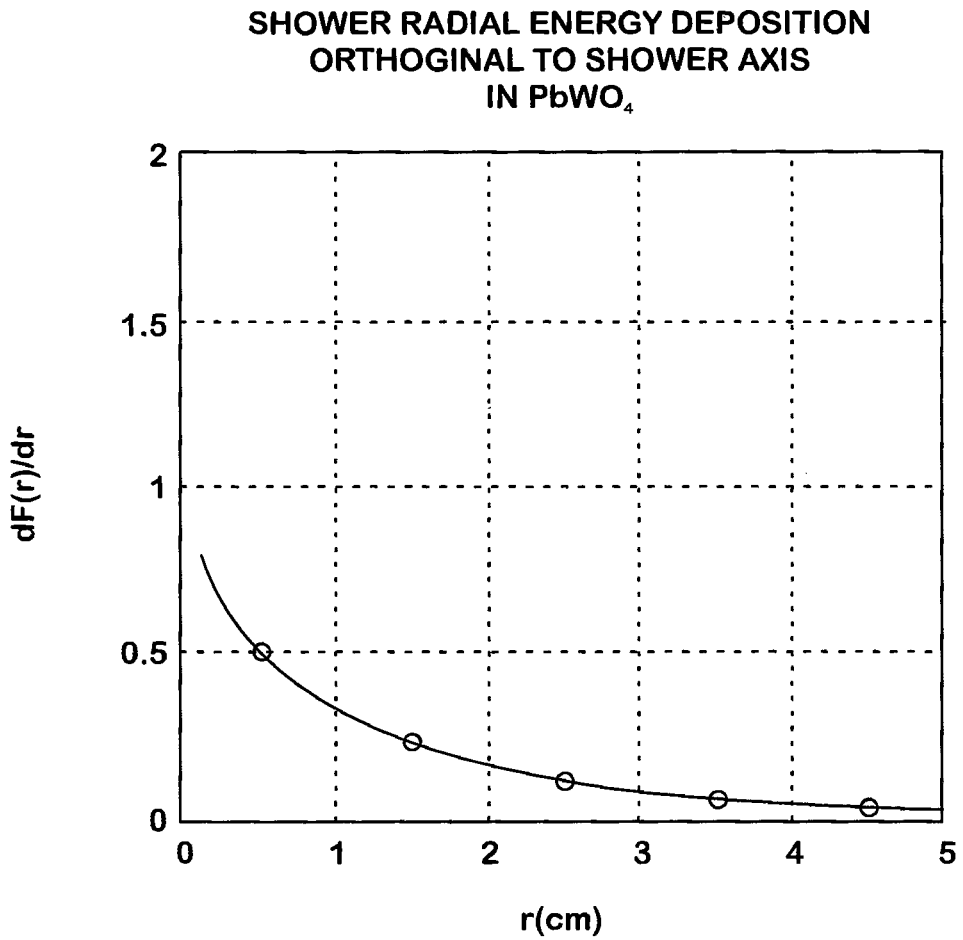
*FIG. 18, which is incorporated by reference from Ser. No. 60/388,428, filed Sep. 29, 2002, is a chart showing shower radial energy disposition orthogonal to shower axis in $PbWO_4$.*

*In FIG. 18, the radial distribution of energy relative to the shower axis for PbWO4 is shown. This material is a scintillator, see table 3 for some of its properties. The radiation length of PbWO4 is 2.7× larger than that of tungsten. One could use a 9×9×9 mm3 in a matrix or a crossed 9×9×200 mm3 hodoscope's sensor array to sample the shower charged particles. These two detector alternatives would have to be studied and compared before one could decide on the better choice. In each case, one would tag the charged particles in an active layer before the shower detector. Either case would be better than using the charged particle tracks.*

*One important consideration, which favors smaller shower localization of tungsten over PbWO4, is its ability to separate the gamma pair of the 0 decay. The opening angle of the gamma pair from the 0 decay is given in the laboratory reference frame as:*

$$\cos\phi = 1-(1+R)^2/2R\gamma^2$$

*where*

$R=E_1/E_2,\ R\leq 1$ $\gamma=E_\pi/m_\pi$

Figure 19:
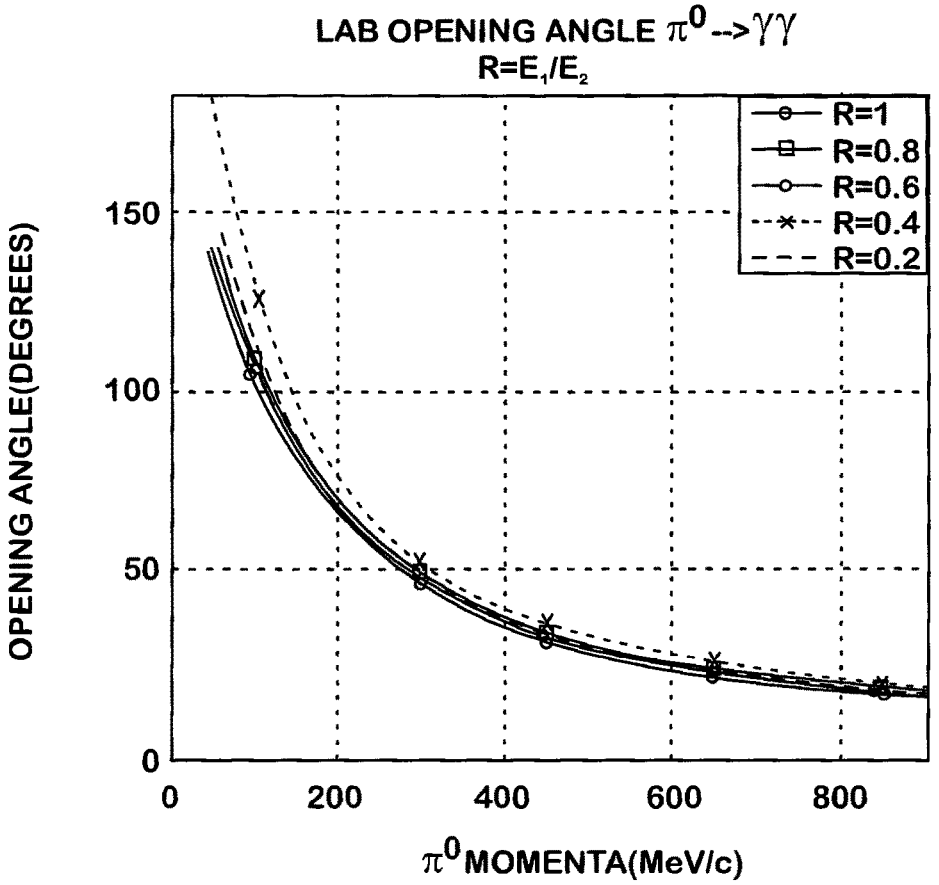
*FIG. 19, which is incorporated by reference from Ser. No. 60/388,428, filed Sep. 29, 2002, is a chart showing the lab opening angle in degrees as a function of neutral pion momenta and the ratio of gamma-ray energies.*
Figure 20:
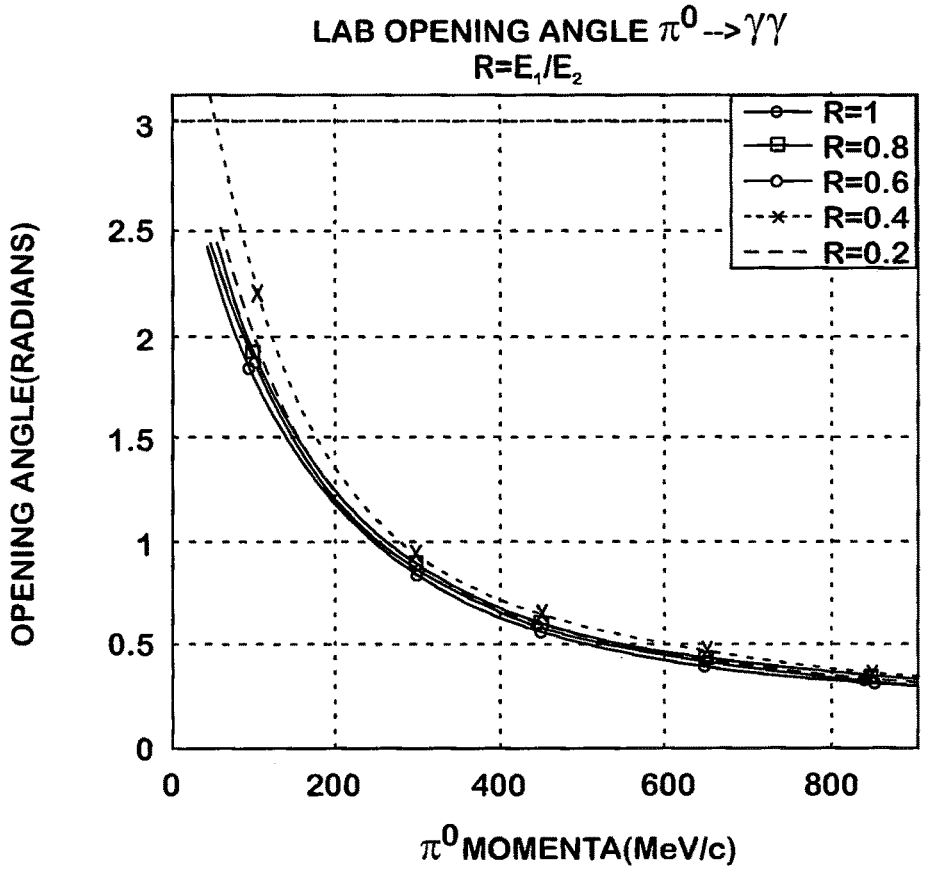
*FIG. 20, which is incorporated by reference from Ser. No. 60/388,428, filed Sep. 29, 2002, is a chart of the lab opening angle in radians for the decay gammas from the neutral pion as a function of pion momentum and the ratio of the energies of the decay gammas.*

*The opening angle of the neutral pion decay is plotted as a function of the 0 momentum. See FIGS. 19 and 20.*

*The smallest opening angle we should expect is 16 degrees (5 cm separation at 15 cm from annihilation site). However, the average opening angle will be around 40 degrees (9 cm separation at 15 cm from the annihilation site). The PbWO4 would loose some efficiency in separating the decay gammas as compared to the tungsten shower detector at the higher pion momenta.*

*It should be clear that a shower detector would be quite massive (>400 lbs for steradians).*

*Two techniques for localizing the proton-antiproton annihilation site have been examined for the case where the site is at the center of a 30 cm diameter sphere of water. Tracking charged pions beyond the sphere is limited to >1.5 mm precision on the vertex reconstruction due to multiple scattering in traversing the 15 cm of water. Pointing of the shower axis from neutral pion decays is expected to yield a vertex localization precision of <0.5 mm. The shower detection can be done using fast scintillator <<15 ns) allowing a faster response than the charged particle tracking.*

What is claimed is:

1. A method for using a synchrotron, the method comprising the steps of: [providing] *altering* a synchrotron designed to accelerate a hadron beam *from initial momentum* to higher [momenta; altering said synchrotron] *momentum* to enable deceleration of *the* hadron [beams] *beam* to lower [momenta] *momentum than said initial momentum by using a radio-frequency acceleration system to impose momentum reduction on the hadron beam*; and using the *altered* synchrotron in [said altering step in] decelerating the hadron beam [to lower momenta].

2. The method of claim 1, wherein the step of altering includes modifying a dipole power supply system of the synchrotron to maintain a bending magnetic field during the decelerating of the hadron beam.

3. The method of claim 1, wherein the step of altering includes modifying a quadruple power supply system of the synchrotron to maintain focusing and defocusing magnetic fields during the decelerating of the hadron beam.

4. The method of claim 1, wherein the step of altering includes modifying a sextuple power supply system of the synchrotron to maintain chromaticity control during the decelerating of the hadron beam.

5. The method of claim 1, wherein the step of altering includes modifying a dipole corrector power supply system of the synchrotron to maintain a trajectory correction magnetic field during the decelerating of the hadron beam.

6. The method of claim 1, wherein the step of altering includes modifying a radio frequency acceleration system of the synchrotron to impose phase stable momentum reduction during the decelerating of the hadron beam.

7. The method of claim 1, wherein the step of altering includes modifying a computer control system of the synchrotron to enable the decelerating of the hadron beam.

8. The method of claim 1, wherein the step of decelerating is carried out with said hadron beam including protons.

9. The method of claim 1, wherein the step of decelerating is carried out with said hadron beam including antiprotons.

10. The method of claim 1, wherein the step of decelerating is carried out with said hadron beam including atomic ions.

11. The method of claim 2, wherein the step of modifying includes adding a dipole power supply component to ensure that electrical current from the dipole power supply system follows commands from a computer control system.

12. The method of claim 2, wherein the step of modifying includes removing a dipole power supply component to ensure that electrical current from the dipole power supply system follows commands from a computer control system.

13. The method of claim 2, wherein the step of modifying includes altering a dipole power supply component to ensure that electrical current from the dipole power supply system follows commands from a computer control system.

14. The method of claim 2, wherein the step of modifying includes adding a computer control system component to direct the dipole power supply system to follow the commands from said computer control system.

15. The method of claim 2, wherein the step of modifying includes removing a computer control system component to direct the dipole power supply system to follow commands from said computer control system.

16. The method of claim 2, wherein the step of modifying includes altering a computer control system component to direct the dipole power supply system to follow commands from said computer control system.

17. The method of claim 2, wherein the step of modifying includes altering a value of a computer control system database variable to direct the dipole power supply system to follow commands from said computer control system.

18. The method of claim 2, wherein the step of modifying includes altering a byte of information stored in a computer control system component to direct the dipole power supply system to follow commands from said computer control system.

19. The method of claim 2, wherein the step of modifying includes altering a value of a computer control system variable to direct the dipole power supply system to follow commands from said computer control system.

20. The method of claim 3, wherein step of modifying includes adding a quadruple power supply component to ensure that electrical current from the quadruple power supply system follows commands from a computer control system.

21. The method of claim 3, wherein the step of modifying includes removing a quadruple power supply component to ensure that electrical current from the quadruple power supply system follows commands from a computer control system.

22. The method of claim 3, wherein the step of modifying includes altering a quadruple power supply component to ensure that electrical current from the power supply follows commands from a computer control system.

23. The method of claim 3, wherein the step of modifying includes adding a computer control system component to direct the quadruple power supply system to follow the commands from said computer control system.

24. The method of claim 3, wherein the step of modifying includes removing a computer control system component to direct the quadruple power supply system to follow commands from said computer control system.

25. The method of claim 3, wherein the step of modifying includes altering a computer control system component to direct the quadruple power supply system to follow commands from said computer control system.

26. The method of claim 3, wherein the step of modifying includes altering a value of a computer control system database variable to direct the quadruple power supply system to follow commands from said computer control system.

27. The method of claim 3, wherein the step of modifying includes altering a byte of information stored in a computer control system component to direct the quadruple power supply system to follow commands from said computer control system.

28. The method of claim 3, wherein the step of modifying includes altering a value of a computer control system variable to direct the quadruple power supply system to follow commands from said computer control system.

29. The method of claim 4, wherein step of modifying includes adding a sextuple power supply component to ensure that electrical current from the sextuple power supply system follows commands from a computer control system.

30. The method of claim 4, wherein the step of modifying includes removing a sextuple power supply component to ensure that electrical current from the sextuple power supply system follows commands from a computer control system.

31. The method of claim 4, wherein the step of modifying includes altering a sextuple power supply component to ensure that electrical current from the sextuple power supply system follows commands from a computer control system.

32. The method of claim 4, wherein the step of modifying includes adding a computer control system component to direct the sextuple power supply system to follow the commands from said computer control system.

33. The method of claim 4, wherein the step of modifying includes removing a computer control system component to direct the sextuple power supply system to follow commands from said computer control system.

34. The method of claim 4, wherein the step of modifying includes altering a computer control system component to direct the sextuple power supply system to follow commands from said computer control system.

35. The method of claim 4, wherein the step of modifying includes altering a value of a computer control system database variable to direct the sextuple power supply system to follow commands from said computer control system.

36. The method of claim 4, wherein the step of modifying includes altering a byte of information stored in a computer control system component to direct the sextuple power supply system to follow commands from said computer control system.

37. The method of claim 4, wherein the step of modifying includes altering a value of a computer control system variable to direct the sextuple power supply system to follow commands from said computer control system.

38. The method of claim 5, wherein step of modifying includes adding a dipole corrector power supply component to ensure that electrical current from the dipole corrector power supply system follows commands from a computer control system.

39. The method of claim 5, wherein the step of modifying includes removing a dipole corrector power supply component to ensure that electrical current from the dipole corrector power supply system follows commands from a computer control system.

40. The method of claim 5, wherein the step of modifying includes altering a dipole corrector power supply component to ensure that electrical current from the dipole corrector power supply system follows commands from a computer control system.

41. The method of claim 5, wherein the step of modifying includes adding a computer control system component to direct the dipole corrector power supply system to follow the commands from said computer control system.

42. The method of claim 5, wherein the step of modifying includes removing a computer control system component to direct the dipole corrector power supply system to follow commands from said computer control system.

43. The method of claim 5, wherein the step of modifying includes altering a computer control system component to direct the dipole corrector power supply system to follow commands from said computer control system.

44. The method of claim 5, wherein the step of modifying includes altering a value of a computer control system database variable to direct the dipole corrector power supply system to follow commands from said computer control system.

45. The method of claim 5, wherein the step of modifying includes altering a byte of information stored in a computer control system component to direct the dipole corrector power supply system to follow commands from said computer control system.

46. The method of claim 5, wherein the step of modifying includes altering a value of a computer control system variable to direct the dipole corrector power supply system to follow commands from said computer control system.

47. The method of claim 6, wherein step of modifying includes adding a radio frequency acceleration system component to ensure that an electromagnetic field of said radio frequency acceleration system follows commands from a computer control system.

48. The method of claim 6, wherein the step of modifying includes removing a radio frequency acceleration system component to ensure that an electromagnetic field of said radio frequency acceleration system follows commands from a computer control system.

49. The method of claim 6, wherein the step of modifying includes altering a radio frequency acceleration system component to ensure that an electromagnetic field of said radio frequency acceleration system follows commands from a computer control system.

50. The method of claim 6, wherein the step of modifying includes adding a computer control system component to direct the radio frequency acceleration system to follow the commands from said computer control system.

51. The method of claim 6, wherein the step of modifying includes removing a computer control system component to direct the radio frequency acceleration system to follow commands from said computer control system.

52. The method of claim 6, wherein the step of modifying includes altering a computer control system component to direct the radio frequency acceleration system to follow commands from said computer control system.

53. The method of claim 6, wherein the step of modifying includes altering a value of a computer control system database variable to direct the radio frequency acceleration system to follow commands from said computer control system.

54. The method of claim 6, wherein the step of modifying includes alerting a byte of information stored in a computer control system component to direct the radio frequency acceleration system to follow commands from said computer control system.

55. The method of claim 6, wherein the step of modifying includes altering a value of a computer control system variable to direct the radio frequency acceleration system to follow commands from said computer control system.

*56. A method for using a synchrotron, the method comprising:*

*using the synchrotron to decelerate an antiproton beam to lower momentum;*

*extracting the decelerated antiproton beam from the synchrotron; and*

*delivering the extracted antiproton beam into living tissue.*

*57. The method of claim 56, wherein the living tissue comprises cancerous cells.*

*58. The method of claim 56, wherein nuclei in the living tissue is partially transmuted via antiproton annihilations into radioisotopes.*

*59. The method of claim 58, wherein the radioisotopes are used in imaging techniques.*

*60. The method of claim 58, wherein the radioisotopes are used for therapeutic treatment.*

*61. A method for treating a patient having a plurality of undesirable cells, the method comprising:*

*creating an antiproton beam at an energy higher than a predetermined therapeutic energy level;*

*decelerating said antiproton beam to a predetermined, therapeutic energy level, said decelerating using a radio-frequency acceleration system to impose momentum reduction;*

*exposing at least a portion of the plurality of undesirable cells to said beam;*

*generating radioisotopes within the plurality of undesirable cells by said exposing; and*

*monitoring the decay radiation from said radioisotopes.*

*62. The method of claim 61, wherein the cells are cancerous.*

*63. A method for treating a patient, the method comprising:*

*creating an antiproton beam at an energy higher than a predetermined irradiation energy level;*

*decelerating said antiproton beam to the predetermined irradiation energy level, said decelerating using a radio-frequency acceleration system to impose momentum reduction;*

*exposing at least a portion of the patient body to said antiprotons at the predetermined irradiation energy level;*

*generating radioisotopes within said body by said exposing; and*

*providing patient therapy with said radioisotopes.*

*64. A method for imaging a patient, the method comprising:*

*creating an antiproton beam at an energy higher than a predetermined irradiation energy level;*

*decelerating said antiproton beam to the predetermined irradiation energy level, said decelerating using a radio-frequency acceleration system to impose momentum reduction;*

*exposing at least a portion of the patient body to said antiproton beam at the predetermined irradiation energy level;*

*generating radioisotopes within said body by said exposing; and*

*providing patient imaging with said radioisotopes.*

*65. The method of claim 1, wherein the hadron beam at the lower momenta comprises a decelerated antiproton beam, and further including:*

*extracting the decelerated antiproton beam from the synchrotron; and*

*delivering the extracted antiproton beam into living tissue.*

*66. The method of claim 1, wherein the step of using the synchrotron includes creating an antiproton beam at an energy higher than a predetermined therapeutic energy level, and the step of decelerating includes decelerating said antiprotons to a predetermined, therapeutic energy level; and further comprising:*

*exposing at least a portion of a plurality of undesirable cells to said beam of antiprotons;*

*generating radioisotopes within the plurality of undesirable cells by said exposing; and*

*monitoring the decay radiation from said radioisotopes.*

*67. The method of claim 1, wherein the step of using the synchrotron includes creating an antiproton beam at an energy higher than a predetermined irradiation energy level, and the decelerating includes decelerating said antiproton beam to the predetermined, irradiation energy level; and further comprising:*

*exposing at least a portion of the patient body to said antiproton beam at the predetermined irradiation energy level;*

*generating radioisotopes within said body by said exposing; and*

*providing patient imaging with said radioisotopes.*

* * * * *